United States Patent [19]
Rampulla et al.

[11] Patent Number: 6,140,270
[45] Date of Patent: Oct. 31, 2000

[54] PROCESS FOR THE PREPARATION OF 6-(PERFLUOROALKYL) URACIL COMPOUNDS FROM 2-(N,N-DISUBSTITUTED) AMINO-4-(PERFLUOROALKYL)-1,3-OXAZIN-6-ONE COMPOUNDS

[75] Inventors: Richard Anthony Rampulla, Whitehouse Station; Venkataraman Kameswaran, Trenton; Peter John Wepplo, Princeton, all of N.J.

[73] Assignee: American Cyanamid Company

[21] Appl. No.: 09/251,286

[22] Filed: Feb. 16, 1999

Related U.S. Application Data

[63] Continuation-in-part of application No. 09/152,524, Sep. 14, 1998.

[51] Int. Cl.[7] ............ A01N 43/54; C07D 239/00; C07D 417/00
[52] U.S. Cl. ............ 504/239; 504/242; 504/243; 544/245; 544/310
[58] Field of Search ............ 544/245, 310; 504/239, 242, 243

[56] References Cited

U.S. PATENT DOCUMENTS 5,523,278  6/1996  Wepplo .................. 504/271

FOREIGN PATENT DOCUMENTS 197 50 195  5/1999  Germany.

OTHER PUBLICATIONS

M. Decock–Plancquaert et al., Bull. Soc. Chim. Belg., 101(4), pp. 313–321 (1992).

*Primary Examiner*—Mukund J. Shah
*Assistant Examiner*—Sudhaker B Patel
*Attorney, Agent, or Firm*—Joseph M. Mazzarese; Barbara V. Maurer

[57] ABSTRACT

An improved process for the preparation of 6-(perfluoroalkyl)uracil compounds having the structural formula I

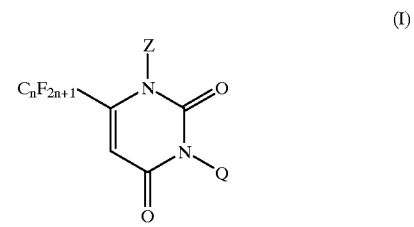

from 2-(N,N-disubstituted)amino-4-(perfluoroalkyl)-1,3-oxazin-6-one compounds having the structural formula II

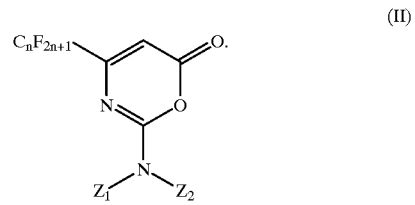

13 Claims, No Drawings

PROCESS FOR THE PREPARATION OF 6-(PERFLUOROALKYL) URACIL COMPOUNDS FROM 2-(N,N-DISUBSTITUTED) AMINO-4-(PERFLUOROALKYL)-1,3-OXAZIN-6-ONE COMPOUNDS

This is a continuation-in-part of U.S. Ser. No. 09/152,524 filed Sep. 14, 1998, the entire disclosure of which is incorporated by reference herein.

BACKGROUND OF THE INVENTION 6-(Perfluoroalkyl)uracil compounds which are useful as herbicidal agents and methods for their preparation are known in the art.

Although the methods described in the art are useful for the preparation of those compounds, there is ongoing research to discover new and improved methods for the preparation of 6-(perfluoroalkyl)uracil compounds.

It is, therefore, an object of the present invention to provide an improved process for the preparation of 6-(perfluoroalkyl)uracil compounds.

Other objects and advantages of the present invention will be apparent to those skilled in the art from the description below and the appended claims.

SUMMARY OF THE INVENTION

The present invention provides a new process for the preparation of 6-(perfluoroalkyl)uracil compounds having the structural formula I

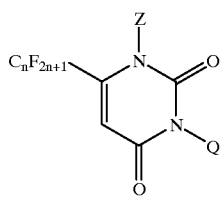

(I)

wherein n is an integer of 1, 2, 3, 4, 5 or 6;

Z is hydrogen or $C_1$–$C_6$alkyl; and

Q is a $C_1$–$C_6$alkyl group or an optionally substituted phenyl, benzyl, heteroaryl or methyleneheteroaryl group, which process comprises:
(a) reacting a 2-(N,N-disubstituted)amino-4-(perfluoroalkyl)-1,3-oxazin-6-one compound having the structural formula II

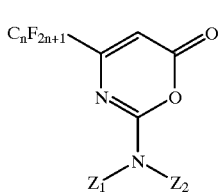

(II)

wherein $Z_1$ and $Z_2$ are each independently $C_1$–$C_8$alkyl or $Z_1$ and $Z_2$ may be taken together with the atom to which they are attached to form a 4- to 7-membered ring wherein $Z_1Z_2$ is represented by —$(CH_2)_2O\ (CH_2)_2$— or —$(CH_2)_m$— where m is an integer of 3, 4, 5 or 6; and n is as described above, with an amine compound having the structural formula III $QNH_2$ (III)

wherein Q is as described above in the presence of an acid or base to form the 6-(perfluoroalkyl)uracil compound of formula I wherein Z is hydrogen; and (b) optionally alkylating the formula I compound wherein Z is hydrogen to form a formula I compound wherein Z is $C_1$–$C_6$ alkyl.

DETAILED DESCRIPTION OF THE INVENTION

In a preferred embodiment of the present invention, the 2-(N,N-disubstituted)amino-4-(perfluoroalkyl)-1,3-oxazin-6-one compound of formula II is reacted with the amine compound of formula III and the acid or base, preferably at a temperature ranging from about 20° C. to 150° C., in the presence of a solvent.

In a more preferred embodiment of this invention, the 2-(N,N-disubstituted)amino-4-(perfluoroalkyl)-1,3-oxazin-6-one compound is reacted with the amine compound and the acid, preferably at a temperature ranging from about 20° C. to 150° C., in the presence of a solvent.

Acids suitable for use in this invention include organic acids including, but not limited to, $C_1$–$C_6$alkanoic acids such as formic acid, acetic acid, propionic acid and the like; and mineral acids including, but not limited to, hydrochloric acid, sulfuric acid, phosphoric acid and the like. Preferred acids include acetic acid and propionic acid.

Bases suitable for use in the preparation of the formula I compounds include, but are not limited to, tri($C_1$–$C_6$alkyl) amines such as trimethylamine, triethylamine, tripropylamine, tributylamine, diisopropylethylamine and the like; heterocyclic tertiary amines such as 1,8-diazazbicyclo[5.4.0]undec-7-ene (DBU), 1,5-diazabicyclo[4.3.0]non-5-ene (DBN), 1,4-diazabicyclo[2.2.2]octane, pyridine, substituted pyridines, quinoline, substituted quinolines and the like; and alkali metal $C_1$–$C_6$alkoxides such as potassium tert-butoxide, sodium tert-butoxide and the like. Preferred second bases include 1,8-diazabicyclo[5.4.0]-undec-7-ene and 1,5-diazabicyclo[4.3.0]non-5-ene.

Solvents suitable for use in the present invention include, but are not limited to, carboxylic acid amides such as N,N-dimethylformamide, N,N-dimethylacetamide and the like; dialkyl sulfoxides such as dimethyl sulfoxide and the like; aromatic hydrocarbons such as toluene, benzene, xylenes, mesitylene and the like; halogenated aromatic hydrocarbons such as chlorobenzene, fluorobenzene and the like; aliphatic hydrocarbons such as pentane, hexane, heptane and the like; halogenated aliphatic hydrocarbons such as methylene chloride, chloroform, carbon tetrachloride, 1,2-dichloroethane and the like; alkanoic acids such as formic acid, acetic acid, propionic acid and the like; ketones such as acetone, methyl ethyl ketone and the like; ethers such as diethyl ether, tetrahydrofuran, dioxane, 1,2-dimethoxyethane and the like; nitriles such as acetonitrile, propionitrile and the like; and water; and mixtures thereof. It should be understood that a solvent should be chosen which does not adversely react with the particular acid or base being used. For example, an alkanoic acid would generally not be chosen as the solvent when the base is present. It should also be understood that when an acid is present, the acid may also serve as the solvent. For example, an alkanoic acid such as acetic acid, propionic acid and the like may serve as both the acid and the solvent in step (a) of the process of the present invention.

Alkylation procedures suitable for use in this invention include conventional procedures known in the art. In a preferred embodiment of this invention, the alkylation procedure comprises reacting the formula I compound wherein Z is hydrogen with an alkyl halide having the structural formula IV or a dialkylsulfate ester having the structural formula V in the presence of a base $$XZ \quad (IV)$$

or $$Z O \overset{O}{\underset{O}{\overset{\parallel}{S}}} O Z \quad (V)$$

wherein X is chlorine, bromine or iodine, and Z is $C_1$–$C_6$alkyl.

Bases suitable for use in the alkylation procedures of this invention include conventional bases known in the art including, but not limited to, alkali metal hydrides such as sodium hydride and the like; alkali metal $C_1$–$C_6$alkoxides such as potassium tert-butoxide, sodium tert-butoxide and the like; alkali metal hydroxides such as potassium hydroxide, sodium hydroxide and the like; alkali metal carbonates such as sodium carbonate, potassium carbonate and the like; alkaline earth metal hydroxides such as calcium hydroxide and the like; and alkaline earth metal carbonates such as calcium carbonate and the like.

Preferred formula II compounds for use in the process of this invention are those wherein n is 1; and $Z_1$ and $Z_2$ are each independently $C_1$–$C_6$alkyl.

More preferred formula II compounds for use in the preparation of 6-(trifluoromethyl)uracil compounds are those wherein n is 1; and $Z_1$ and $Z_2$ are the same and represent methyl or ethyl.

Preferred formula I compounds which may be prepared by the process of the present invention are those wherein n is 1;

Z is hydrogen or $C_1$–$C_4$alkyl;

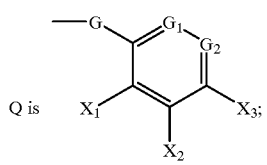

G is $CH_2$ or a bond;

$G_1$ is $CX_5$ or N;

$G_2$ is $CX_4$ or N;

$X_1$ is hydrogen, halogen or a $C_1$–$C_6$alkyl group optionally substituted with one epoxy group, $X_2$ is hydrogen, halogen $NRR_1$, $CO_2R_2$, $C(O)R_3$, $OR_4$, $SO_2R_5$, $SO_2NR_6R_7$, $C(R_8)(OR_9)_2$, $C(R_{10})$=$NOR_{11}$, $C(R_{12})$=$C(R_{13})$—$C(OR_{14})$=$NOR_{15}$, $CH_2O$—$NCO_2R_{16}$, 1,3-dioxolane optionally substituted with one $C_1$–$C_6$alkoxy group or one or two $C_1$–$C_4$alkyl groups, 1,3-dioxolinone optionally substituted with one $C_1$–$C_6$alkoxy group or one or two $C_1$–$C_4$alkyl groups, or $C_1$–$C_4$alkyl optionally substituted with one $CO_2R_2$ group and one halogen atom, and $X_3$ is hydrogen, halogen, $C_1$–$C_4$haloalkyl, $CO_2R_{17}$, cyano, $C_1$–$C_4$haloalkoxy, $OR_{18}$ or $C_1$–$C_4$alkyl, or when $X_1$ and $X_2$ are taken together with the atoms to which they are attached, they may form a five- or six-membered ring wherein $X_1X_2$ or $X_2X_1$ is represented by:

—$OC(R_{20})(R_{21})O$—, —$CH_2S(O)_pN(R_{22})$—, —$SC(R_{23})$=$N$—, —$CH$=$CH$—$CH(R_{11})O$—, —$OC(O)N$—, —$SC(R_{24})$=$N$—, —$ON(R_{25})C(O)$—, —$OC(CO_2R_{26})$=$C(R_{27})$—, —$NC(R_{28})$=$C(SR_{29})$—, —$CH$=$C(CO_2R_{30})O$—, —$CH_2CH(R_{31})O$— or —$OC(R_{32})(R_{33})C(O)$—, or when $X_2$ and $X_3$ are taken together with the atoms to which they are attached, they may form a five- or six-membered ring wherein $X_2X_3$ or $X_3X_2$ is represented by:

—$NC(R_{34})$=$NC(S)$—, —$N(R_{35})N$=$C(R_{36})$—, —$N(R_{37})C(R_{38})$=$N$—, —$N(R_{38})C(O)CH_2O$—, —$N(R_{39})C(O)CH$=$CH$—, —$S$—$N$=$C(R_{40})$—, —$O$—$N$=$C(R_{41})$—, —$N$=$N$—$N(R_{42})$—, —$C(R_{43})(R_{44})C(O)N(R_{45})$— or —$N(R_{46})C(O)C(R_{47})(R_{48})$—;

$X_4$ is hydrogen, halogen or $OR_{19}$;

$X_5$ is hydrogen or halogen;

R, $R_{56}$, $R_{64}$, $R_{69}$, $R_{70}$, $R_{77}$ and $R_{91}$ are each independently hydrogen, $SO_2R_{49}$, $C_1$–$C_4$alkyl, $C_3$–$C_7$cycloalkyl, $C_3$–$C_6$alkenyl, $C_3$–$C_6$alkynyl, phenyl or benzyl;

$R_1$ is hydrogen, $SO_2R_{50}$, $C(O)R_{51}$, amino or $C_1$–$C_4$alkyl optionally substituted with $CO_2R_{52}$ or $C(O)R_{53}$;

$R_2$, $R_{16}$, $R_{17}$, $R_{26}$, $R_{30}$, $R_{68}$, $R_{75}$, $R_{76}$, $R_{82}$ and $R_{88}$ are each independently hydrogen, $C_1$–$C_8$haloalkyl, $C_3$–$C_8$alkenyl, $C_3$–$C_6$alkynyl, phenyl, benzyl, furfuryl, pyridyl, thienyl, $C_1$–$C_8$alkyl optionally substituted with $CO_2R_{54}$, morpholine or $C(O)R_{55}$, or an alkali metal, an alkaline earth metal, ammonium or organic ammonium cation;

$R_3$, $R_{66}$, $R_{67}$, $R_{81}$, $R_{85}$ and $R_{89}$ are each independently hydrogen, $C_1$–$C_6$alkyl, $C_3$–$C_6$alkenyl, $C_3$–$C_6$alkynyl, $NR_{56}R_{57}$, phenyl or benzyl;

$R_4$, $R_{18}$, $R_{19}$ and $R_{65}$ are each independently hydrogen, $C_1$–$C_6$alkyl, $C_3$–$C_6$alkenyl, $C_3$–$C_6$alkynyl, $C_1$–$C_4$haloalkyl, $C(O)R_{58}$, $C(S)R_{59}$ or benzyl;

$R_5$ and $R_{72}$ are each independently $C_1$–$C_6$alkyl, $C_1$–$C_6$haloalkyl, $NR_{60}R_{61}$, imidazole or indazole;

$R_6$, $R_{11}$, $R_{12}$, $R_{14}$, $R_{15}$, $R_{20}$, $R_{21}$, $R_{22}$, $R_{25}$, $R_{28}$, $R_{29}$, $R_{31}$, $R_{32}$, $R_{33}$, $R_{35}$, $R_{45}$, $R_{46}$, $R_{63}$ and $R_{80}$ are each independently hydrogen or $C_1$–$C_4$alkyl;

$R_7$ is hydrogen, $C_3$–$C_6$alkenyl, $C_3$–$C_6$alkynyl, benzyl, or $C_1$–$C_4$alkyl optionally substituted with cyano or $C(O)R_{62}$;

$R_8$ and $R_{27}$ are each independently hydrogen, $C_1$–$C_4$alkyl or $C_1$–$C_4$alkoxy;

$R_9$ and $R_{90}$ are each independently $C_1$–$C_6$alkyl;

$R_{10}$ is hydrogen, $C_1$–$C_6$alkyl, phenyl or benzyl;

$R_{13}$, $R_{24}$ and $R_{36}$ are each independently hydrogen, $C_1$–$C_6$alkyl or halogen;

$R_{23}$ is hydrogen or $NR_{63}R_{64}$;

$R_{34}$ is hydrogen, $C_1$–$C_4$alkyl or $C_1$–$C_4$haloalkyl;

$R_{37}$ is hydrogen, $C_1$–$C_4$alkyl or $C_2$–$C_8$alkoxyalkyl;

$R_{38}$ and $R_{39}$ are each independently hydrogen, $C_1$–$C_4$alkyl, $C_1$–$C_4$haloalkyl, $C_3$–$C_6$alkenyl or $C_3$–$C_6$alkynyl;

$R_{40}$, $R_{41}$ and $R_{42}$ are each independently hydrogen, halogen, cyano, $OR_{65}$, $C(O)R_{66}$, $C(S)R_{67}$, $CO_2R_{68}$, $C(=NOR_{69})$,
- a $C_1$–$C_8$alkyl, $C_3$–$C_7$cycloalkyl, $C_2$–$C_8$alkenyl or $C_2$–$C_8$alkynyl group, wherein each group is optionally substituted with any combination of one to six halogen atoms, one to three $C_1$–$C_{10}$-alkoxy groups, one or two $C_1$–$C_6$haloalkoxy groups, one or two $NR_{70}R_{71}$ groups, one or two $S(O)_qR_{72}$ groups, one or two cyano groups, one or two $C_3$–$C_7$cycloalkyl groups, one $OSO_2R_{73}$ group, one or two $C(O)R_{74}$ groups, one or two $CO_2R_{75}$ groups, one or two $C(O)SR_{76}$ groups, one or two $C(O)NR_{77}R_{78}$ groups, one to three $OR_{79}$ groups, one or two $P(O)(OR_{80})_2$ groups, one 1,3-dioxolane optionally substituted with one to three $C_1$–$C_4$alkyl groups, or one 1,3-dioxane optionally substituted with one to three $C_1$–$C_4$alkyl groups, or
- phenyl or benzyl optionally substituted with any combination of one to three halogen atoms, one to three $C_1$–$C_6$alkyl groups, one to three $C_1$–$C_6$alkoxy groups, one $C_3$–$C_7$cycloalkyl group, one $C_1$–$C_4$haloalkyl group, one $C_1$–$C_4$alkylthio group, one cyano group, one nitro group, one $C(O)R_{81}$ group, one $CO_2R_{82}$ group, one $OR_{83}$ group, one $SR_{84}$ group, one $C_1$–$C_6$alkoxymethyl group, one hydroxymethyl group, one $C_3$–$C_8$alkenyloxymethyl group, or one $C_1$–$C_8$haloalkoxymethyl group;

$R_{43}$, $R_{44}$, $R_{47}$ and $R_{48}$ are each independently hydrogen, $C_1$–$C_4$alkyl, $C_1$–$C_4$haloalkyl, $C_3$–$C_6$alkenyl, $C_3$–$C_6$alkynyl or $C_3$–$C_7$cycloalkyl, or $R_{43}$ and $R_{44}$ or $R_{47}$ and $R_{48}$ may be taken together with the atom to which they are attached to form a $C_3$–$C_7$cycloalkyl group;

$R_{49}$, $R_{50}$ and $R_{86}$ are each independently $C_1$–$C_6$alkyl, $NR_{93}R_{94}$, $C_1$–$C_4$haloakyl, $C_3$–$C_6$alkenyl, $C_3$–$C_6$alkynyl or benzyl;

$R_{51}$, $R_{52}$, $R_{53}$, $R_{54}$, $R_{55}$, $R_{57}$, $R_{58}$, $R_{59}$, $R_{60}$, $R_{61}$, $R_{62}$, $R_{71}$, $R_{73}$, $R_{74}$, $R_{78}$, $R_{87}$ and $R_{92}$ are each independently hydrogen, $C_1$–$C_6$alkyl, $C_3$–$C_7$cycloalkyl, $C_1$–$C_6$haloalkyl, $C_3$–$C_6$alkenyl, $C_3$–$C_6$alkynyl, phenyl or benzyl;

$R_{79}$, $R_{83}$ and $R_{84}$ are each independently hydrogen, $C(O)R_{85}$, $SO_2R_{86}$, $C_1$–$C_6$haloalkyl, $C_2$–$C_6$alkenyl, $C_5$–$C_8$cycloalkenyl, $C_2$–$C_6$alkynyl, phenyl, benzyl, or $C_1$–$C_{10}$alkyl optionally substituted with one hydroxyl, benzyloxy, $OC(O)R_{87}$, $C_1$–$C_6$alkoxy, $CO_2R_{88}$, $C(O)R_{89}$, $C(OR_{90})_2$, $C(O)NR_{91}R_{92}$ or cyano group;

$R_{93}$ and $R_{94}$ are each independently hydrogen, $C_1$–$C_4$haloalkyl, $C_2$–$C_6$alkenyl, $C_3$–$C_8$cycloalkyl, $C_1$–$C_8$alkyl optionally substituted with one or two $C_1$–$C_4$alkoxy groups or one cyanoalkyl group, or benzyl or phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one cyano group or one nitro group, and
- when $R_{93}$ and $R_{94}$ are taken together with the atom to which they are attached, they form a 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy and $C_1$–$C_4$haloalkylsulfonyl groups; and p and q are each independently 0, 1 or 2; and the optical isomers, diastereomers and/or tautomers thereof.

Of these more preferred formula I compounds, the most preferred are those wherein Z is hydrogen or methyl;

$X_1$ is hydrogen, fluorine or $C_1$–$C_3$alkyl optionally substituted with one epoxy group; or, when $X_1$ and $X_2$ are taken together with the atoms to which they are attached, they may form a five- or six-membered ring wherein $X_1X_2$ or $X_2X_1$ is represented by:
—$OC(R_{20})(R_{21})O$—, —$CH_2S(O)_pN(R_{22})$—, —$SC(R_{23})=N$—, —$CH=CH$—$CH(R_{11})O$—, —$OC(O)N$—, —$SC(R_{24})=N$—, —$ON(R_{25})C(O)$—, —$OC(CO_2R_{26})=CH$—, —$NC(R_{28})=C(SR_{29})$—, —$CH=C(CO_2R_{30})O$—, —$CH_2CH(R_{31})O$— or —$OC(R_{32})(R_{33})C(O)$—;

R, $R_{64}$, $R_{69}$ and $R_{77}$ are each independently hydrogen, $SO_2R_{49}$ or $C_1$–$C_4$alkyl;

$R_2$, $R_{16}$, $R_{17}$, $R_{26}$, $R_{30}$, $R_{68}$, $R_{75}$, $R_{76}$, $R_{82}$ and $R_{88}$ are each independently hydrogen, $C_3$–$C_6$alkenyl or $C_1$–$C_4$alkyl optionally substituted with $CO_2R_{54}$, morpholine or $C(O)R_{55}$;

$R_3$, $R_{66}$, $R_{67}$, $R_{85}$ and $R_{89}$ are each independently hydrogen, $C_1$–$C_4$alkyl or $NR_{56}R_{57}$;

$R_4$, $R_{18}$ and $R_{19}$ are each independently hydrogen, $C_1$–$C_4$alkyl, $C_1$–$C_4$haloalkyl, $C(O)R_{58}$, $C_3$–$C_4$alkenyl or $C_3$–$C_4$alkynyl;

$R_{56}$ is $SO_2R_{49}$;

$R_{57}$ is hydrogen or $C_1$–$C_4$alkyl;

$R_5$ and $R_{72}$ are each independently $NR_{60}R_{61}$ or indazole;

$R_6$, $R_{11}$, $R_{12}$, $R_{14}$, $R_{15}$, $R_{20}$, $R_{21}$, $R_{22}$, $R_{25}$, $R_{28}$, $R_{29}$, $R_{31}$, $R_{32}$, $R_{33}$, $R_{35}$, $R_{45}$, $R_{46}$ and $R_{80}$ are each independently hydrogen or methyl;

$R_7$ is $C_1$–$C_4$alkyl optionally substituted with cyano or $C(O)R_{62}$;

$R_8$ is hydrogen or $C_1$–$C_4$alkoxy;

$R_9$ and $R_{90}$ are each independently $C_1$–$C_4$alkyl;

$R_{10}$ is hydrogen or $C_1$–$C_3$alkyl;

$R_{13}$, $R_{24}$ and $R_{36}$ are each independently hydrogen or chlorine;

$R_{23}$ is $NR_{63}R_{64}$;

$R_{34}$ is $C_1$–$C_3$haloalkyl;

$R_{37}$ is $C_2$–$C_4$alkoxyalkyl;

$R_{38}$ and $R_{39}$ are each independently $C_1$–$C_3$haloalkyl, $C_1$–$C_3$alkyl or propargyl;

$R_{40}$, $R_{41}$ and $R_{42}$ are each independently hydrogen, $C(O)R_{66}$, $C(S)R_{67}$, $CO_2R_{68}$, $C(=NOR_{69})$,
$C_1$–$C_3$alkyl optionally substituted with any combination of one or two halogen atoms, one or two $C_1$–$C_3$alkoxy groups, one or two $C_1$–$C_3$haloalkoxy groups, one $SO_2R_{72}$ group, one or two cyano groups, one $C_3$–$C_5$cycloalkyl group, one $OSO_2R_{73}$ group, one $C(O)R_{74}$ group, one $CO_2R_{75}$ group, one $C(O)SR_{76}$ group, one $C(O)NR_{77}R_{78}$ group, one to two $OR_{79}$ groups, one $P(O)(OR_{80})_2$ group, one 1,3-dioxolane group or one 1,3-dioxane group, or phenyl optionally substituted with any combination of one halogen atom, one or two methyl groups, one methoxy group, one halomethyl group or one $OR_{83}$ group;

$R_{43}$, $R_{44}$, $R_{47}$ and $R_{48}$ are each independently hydrogen or methyl, or $R_{43}$ and $R_{44}$ or $R_{47}$ and $R_{48}$ may be taken together with the atom to which they are attached to form a cyclopropyl group;

$R_{49}$, $R_{50}$ and $R_{86}$ are each independently $C_1$–$C_4$alkyl or $NR_{93}R_{94}$;

$R_{51}$, $R_{52}$, $R_{53}$, $R_{54}$, $R_{55}$, $R_{58}$, $R_{60}$, $R61$, $R_{62}$, $R_{73}$, $R_{74}$, $R_{78}$ and $R_{87}$ are
each independently hydrogen, $C_1$–$C_4$alkyl or $C_1$–$C_4$haloalkyl;

$R_{79}$ and $R_{83}$ are each independently hydrogen, $C(O)R_{85}$, $SO_2R_{86}$, $C_1$–$C_4$haloalkyl, $C_3$–$C_4$alkenyl or
$C_1$–$C_3$alkyl substituted with one $OC(O)R_{87}$, $CO_2R_{88}$, $C(O)R_{89}$, $C(OR_{90})_2$ or cyano group;

$R_{93}$ and $R_{94}$ are each independently hydrogen or $C_1$–$C_8$alkyl; and p is 0, 1 or 2.

The process of the present invention is especially useful for the preparation of 6-(trifluoromethyl)uracil compounds having the structural formula VI

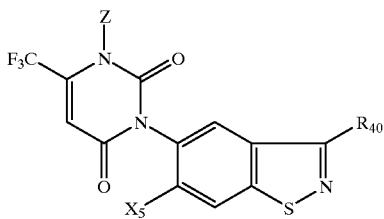

(VI)

wherein

Z is hydrogen or methyl;

$X_5$ is hydrogen or halogen;

$R_{40}$ is hydrogen, $C(O)R_{66}$, $C(S)R_{67}$, $CO_2R_{68}$,
$C_1$–$C_3$alkyl optionally substituted with any combination of one or two halogen atoms, one or two $C_1$–$C_3$alkoxy groups, one or two $C_1$–$C_3$haloalkoxy groups, one $SO_2R_{72}$ group, one or two cyano groups, one $C_3$–$C_5$cycloalkyl group, one $OSO_2R_{73}$ group, one or two $OR_{79}$ groups, one $P(O)(OR_{80})_2$ group, one 1,3-dioxolane group or one 1,3-dioxane group, or
phenyl optionally substituted with any combination of one halogen atom, one or two methyl groups, one methoxy group, one halomethyl group or one $OR_{83}$ group;

$R_{66}$, $R_{67}$, $R_{85}$ and $R_{89}$ are each independently hydrogen, $C_1$–$C_4$alkyl or $NR_{56}R_{57}$;

$R_{56}$ is $SO_2R_{49}$;

$R_{57}$ is hydrogen or $C_1$–$C_4$alkyl;

$R_{49}$ and $R_{86}$ are each independently $C_1$–$C_4$alkyl or $NR_{93}R_{94}$;

$R_{93}$ and $R_{94}$ are each independently hydrogen or $C_1$–$C_8$alkyl;

$R_{68}$ and $R_{88}$ are each independently hydrogen, $C_3$–$C_6$alkenyl or
$C_1$–$C_4$alkyl optionally substituted with $CO_2R_{54}$, morpholine or $C(O)R_{55}$;

$R_{54}$, $R_{55}$, $R_{60}$, $R_{61}$, $R_{73}$ and $R_{87}$ are each independently hydrogen, $C_1$–$C_4$alkyl or $C_1$–$C_4$haloalkyl;

$R_{72}$ is $NR_{60}R_{61}$ or indazole;

$R_{79}$ and $R_{83}$ are each independently hydrogen $C(O)R_{85}$, $SO_2R_{86}$, $C_1$–$C_4$haloalkyl, $C_3$–$C_4$alkenyl or
$C_1$–$C_3$alkyl substituted with one $OC(O)R_{87}$, $CO_2R_{88}$, $C(O)R_{89}$, $C(OR_{90})_2$ or cyano group;

$R_{80}$ is hydrogen or methyl; and $R_{90}$ is $C_1$–$C_4$alkyl.

Exemplary of halogen hereinabove are fluorine, chlorine, bromine and iodine. The terms "halomethyl", "$C_1$–$C_4$haloalkyl", "$C_1$–$C_8$haloalkyl", "$C_1$–$C_3$haloalkoxy", "$C_1$–$C_4$haloalkoxy" and "$C_1$–$C_8$haloalkoxymethyl" are defined as a methyl, $C_1$–$C_4$alkyl, $C_1$–$C_8$alkyl, $C_1$–$C_3$alkoxy, $C_1$–$C_4$alkoxy or $C_1$–$C_8$alkoxymethyl group substituted with one or more halogen atoms. In formula I above, alkali metals include sodium, potassium and lithium, and alkaline earth metals include calcium and magnesium. Organic ammonium cations suitable for use in the present invention include, but are not limited to, a group consisting of a positively charged nitrogen atom joined to from one to four aliphatic groups, each containing from one to sixteen carbon atoms.

In formula I above, 5- to 12-membered monocyclic or fused bicyclic, heterocyclic rings include, but are not limited to, benzimidazole, imidazole, imidazoline-2-thione, indole, isatoic anhydride, morpholine, piperazine, piperidine, purine, pyrazole, pyrrole, pyrrolidine and 1,2,4-triazole rings wherein each ring is optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy, or $C_1$–$C_4$haloalkylsulfonyl groups.

Starting formula II 2-(N,N-disubstituted)amino-4-(perfluoroalkyl)-1,3-oxazin-6-one compounds may be prepared, as shown in Flow Diagram I, by reacting a β-amino-β-(perfluoroalkyl)acrylate compound having the structural formula VII with a phosgeniminium chloride compound having the structural formula VIII (see, Bull. Soc. Chem. Belg., 101(4), pp. 313–321 (1992)).

FLOW DIAGRAM I

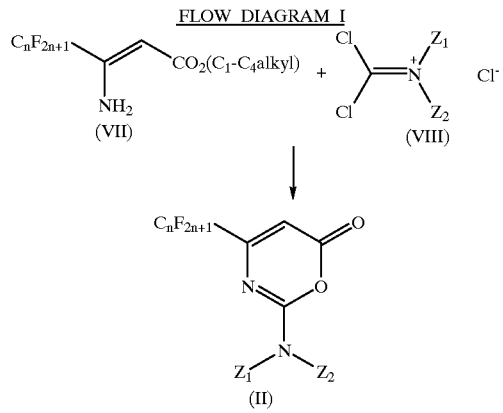

Amine compounds having the structural formula IIIa

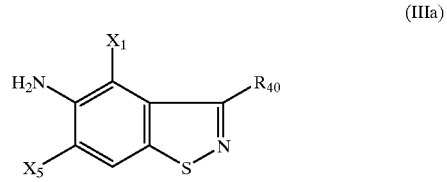

(IIIa)

wherein $X_1$, $X_5$ and $R_{40}$ are as described hereinabove, may be prepared, as shown in Flow Diagram II, by cyclizing a ketone of formula IX with sulfur and ammonium hydroxide or ammonia to form a nitrobenzisothiazole of formula X, and reducing the formula X compound using conventional reducing agents such as iron in acetic acid.

FLOW DIAGRAM II

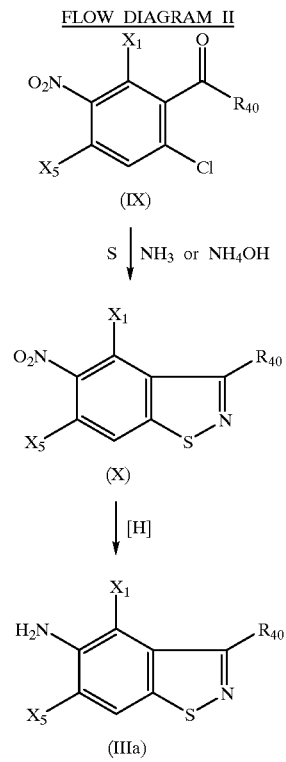

FLOW DIAGRAM III

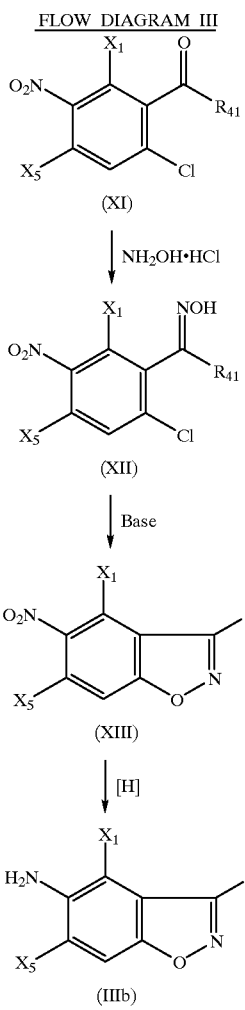

Starting amine compounds having the structural formula IIIb

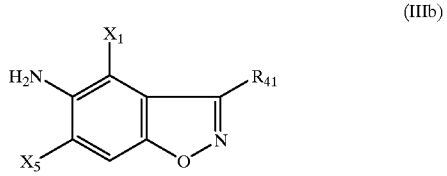

wherein $X_1$, $X_5$ and $R_{41}$ are as described hereinabove, may be prepared, as illustrated in Flow Diagram III, by reacting a ketone of formula XI with hydroxylamine hydrochloride optionally in the presence of sodium acetate to form an oxime of formula XII, cyclizing the formula XII compound with a base such as potassium hydroxide to form a nitrobenzisoxazole of formula XIII, and reducing the formula XIII compound using conventional reducing agents such as tin (II) chloride in acetic acid.

Alternatively, formula XIII nitrobenzisoxazole compounds may be prepared, as shown in Flow Diagram IV, by reacting a ketone of formula XIV with hydroxylamine hydrochloride optionally in the presence of a base such as sodium acetate to form an oxime of formula XV, cyclizing the formula XV compound with 1,1'-carbonyldiimidazole in the presence of a base such as triethylamine to form a benzisoxazole of formula XVI, and nitrating the formula XVI compound using conventional methods such as a nitric acid/sulfuric acid mixture.

FLOW DIAGRAM IV

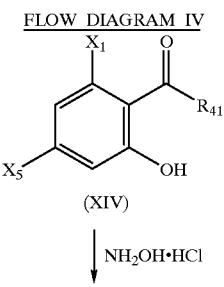

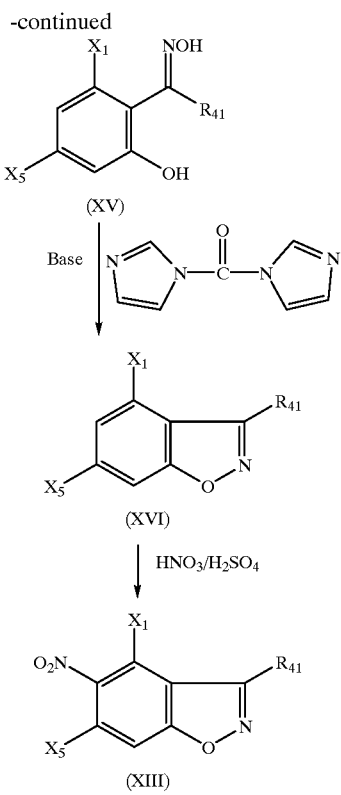

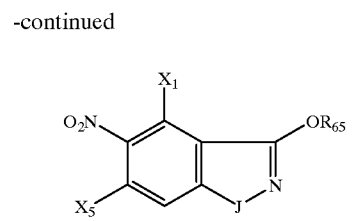

Formula X and XIII intermediate compounds wherein $R_{40}$ and $R_{41}$ are Cl or Br may be prepared, as shown in Flow Diagram VI, by reacting a 5-nitrobenzisoxazol-3-ol or 5-nitrobenzisothiazol-3-ol of formula XVIII with phosphorous oxychloride, phosphorous oxybromide or phosphorous pentabromide.

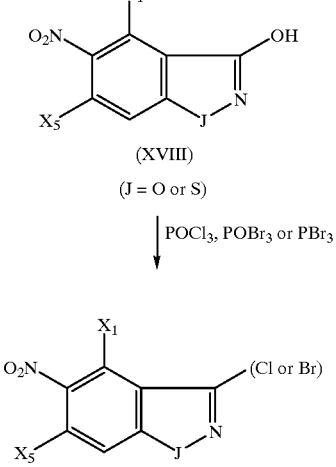

Intermediate compounds of formulas X and XIII wherein $R_{40}$ and $R_{41}$ are $OR_{65}$ may be prepared, as shown in Flow Diagram V, by nitrating a benzisoxazol-3-ol or benzisothiazol-3-ol of formula XVII with a conventional nitrating agent such as a nitric acid/sulfuric acid mixture to form a 5-nitrobenzisoxazol-3-ol or 5-nitrobenzisothiazol-3-ol of formula XVIII, and reacting the formula XVIII compound with an electrophile of formula XIX in the presence of a base such as potassium carbonate.

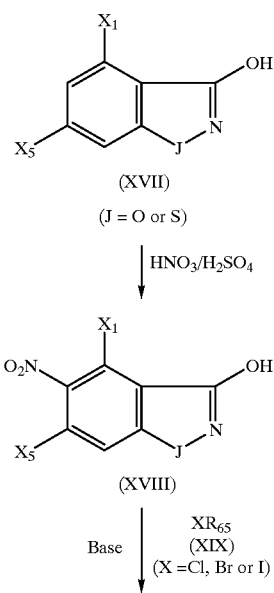

Other methods for the preparation of formula IIIa and IIIb amine compounds will become apparent from the examples set forth below. In addition, certain compounds of formulas IIIa, IIIb, X and XIII may be converted into other compounds of formulas IIIa, IIIb, X and XIII by using conventional procedures known to those skilled in the art.

Other formula III amine compounds are known in the art and may be prepared according to the procedures described in EP 561319-A; EP 540023-A; EP 545206-A; EP 542685-A; EP 473551-A; EP 476697-A; EP 489480-A; EP 496595-A; EP 420194-A; EP 648749-A; EP 705829-A; EP 714602-A; JP 9241245; JP 9301973; U.S. Pat. No. 5,169,430; U.S. Pat. No. 5,310,723; U.S. Pat. No. 5,324,854; U.S. Pat. No. 5,391,541; U.S. Pat. No. 5,399,543; U.S. Pat. No. 5,484,763; U.S. Pat. No. 5,523,278; U.S. Pat. No. 5,602,077; U.S. Pat. No. 5,661,108; WO 93/14073; WO 94/10155; WO 94/24128; WO 91/07393; WO 91/107392; WO 95/04461; WO 95/05079; WO 95/05080; WO 95/17096; WO 95/25725; WO 95/29168; WO 95/32952; WO 95/33746; WO 96/02518; WO 96/08151; WO 96/14315; WO 96/28442; WO 96/34859; WO 96/35679; WO 97/01541; WO 97/01542; WO 97/05118; WO 97/07105; WO 97/08170; WO 97/08171; WO 97/08953; WO 97/12884; WO 97/12886; WO 97/29094; WO 97/29105; WO 97/34484; WO 97/35845; WO 97/42176; WO 97/42188; WO 97/45418; WO 97/47607; WO 98/02422; WO 98/06706; WO 98/08824; WO 98/27057; WO 98/27067; WO 98/27082; and WO 98/27088, among others.

In order to facilitate a further understanding of this invention, the following examples are presented primarily for the purpose of illustrating more specific details thereof. The scope of the invention should not be deemed limited by the examples but encompasses the entire subject matter defined in the claims.

EXAMPLE 1

Preparation of 3-Isopropyl-6-(trifluoromethyl)-2,4 (1H,3H)-pyrimidinedione

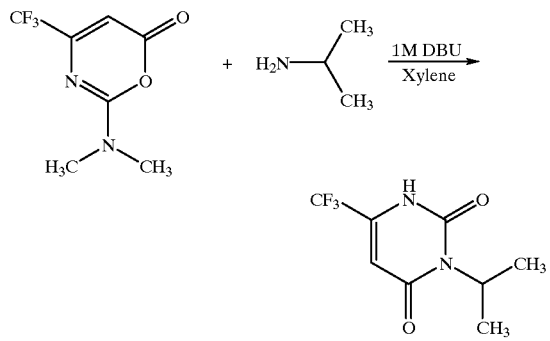

Isopropylamine (1.2 g, 20.3 mmol) and 1,8-diazabicyclo[5,4,0]undec-7-ene (DBU, 6 mL) are added to a solution of 2-dimethylamino-4-trifluoromethyl-6H-1,3-oxazin-6-one (4.0 g, 19.2 mmol) in xylene (34 mL). The resultant reaction mixture is held at 100° C. for 3 hours, cooled, washed with 5 wt. % HCl (40 mL), and extracted with ethyl acetate. The combined organic extracts are concentrated and triturated with heptane. The solids are filtered and dried to give the title product as a yellow powder (2.3 g, 54% yield, mp 127°–129° C.) which is identified by $^1$H NMR (DMSO-$d_6$) δ 6.11 (1H, s), 4.96 (1H, sp), 1.35 (6H, d) ; and $^{19}$F NMR δ −68.9 (s).

Using essentially the same procedure, but using the appropriate amine, the following compounds are obtained:

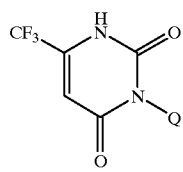

| Q | Acid/Base | Solvent | mp (° C.) | Yield (%) |
|---|---|---|---|---|
| (S)-(+)-CH(CH$_3$)C$_2$H$_5$ | DBU | Xylene | 92–95 | 27 |
| (R)-(−)-CH(CH$_3$)C$_2$H$_5$ | DBU | Xylene | 94–97 | 19 |
| —⟨C$_6$H$_4$⟩—F | CH$_3$CO$_2$H | CH$_3$CO$_2$H | white powder | 47 |
| —⟨C$_6$H$_4$⟩—F | CH$_3$CO$_2$H | Toluene | 169–172 | 74 |
| (5-methyl-3-(2-methoxy-5-methylphenyl)benzo[d]isothiazole) | CH$_3$CO$_2$H | Toluene | 219–222 | 78 |

EXAMPLE 2

Preparation of 3-[3-(6-Methoxy-3,4-xylyl)-1,2-benzisothiazol-5-yl]-6-(trifluoromethyl)-2,4(1H,3H)-pyrimidinedione

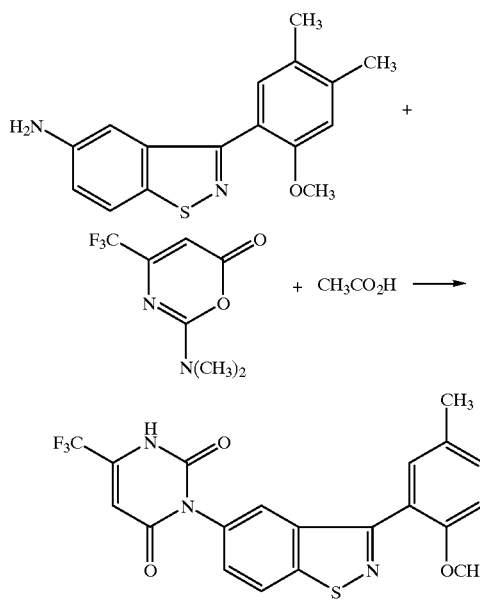

A mixture of 5-amino-3-(6-methoxy-3,4-xylyl)-1,2-benzisothiazole (8.53 g, 30.0 mmol), 2-dimethylamino-4-(trifluoromethyl)-6H-1,3-oxazin-6-one (6.87 g, 33.0 mmol) and acetic acid is refluxed for 2 hours, cooled, and poured into water. The resultant aqueous mixture is filtered to obtain a solid. A solution of the solid in methylene chloride is washed sequentially with water and brine, dried over anhydrous magnesium sulfate, and concentrated in vacuo to obtain an oil. Column chromatography of the oil using silica gel and a 5% diethyl ether in methylene chloride solution gives the title product as a yellow foam (8.37 g, 62.0%) which is identified by NMR spectral analyses.

Using essentially the same procedure, the following compounds are obtained:

| $X_1$ | $X_5$ | $R_{40}$ | mp ° C. |
|---|---|---|---|
| H | H | CN | 255–258 |
| H | H | H | >260 |
| H | H | $CH_3$ | 273–274 |
| H | H | $C_2H_5$ | |
| H | H | 2,5-dimethyl-3-methoxyphenyl | 230–231 |
| H | H | 2,3-dimethyl-4-methoxyphenyl | |
| H | H | 2,5-dimethyl-4-methoxyphenyl | 125–130 |
| H | H | phenyl | >280 |
| H | H | 4-ethylphenyl | 253–254 |
| H | H | 2,5-dimethyl-4-methoxyphenyl | 149–152 |
| H | H | 3-methoxyphenyl | |
| H | H | 2,3,5-trimethyl-4-methoxyphenyl | |

-continued
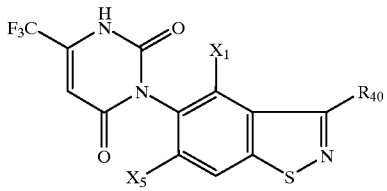
| X₁ | X₅ | R₄₀ | mp °C. |
|---|---|---|---|
| H | H | 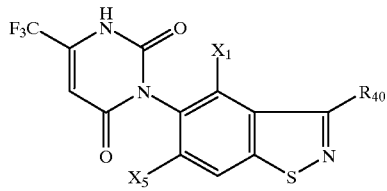 | |
| H | H | 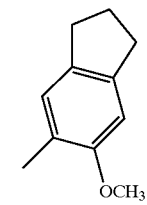 | |
| H | H | 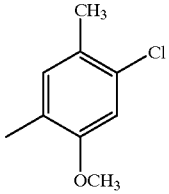 | |
| H | H | 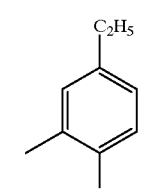 | |
| H | H | 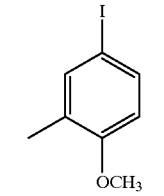 | |
| H | H | 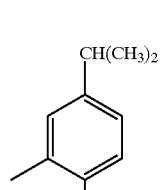 | |
| H | H | 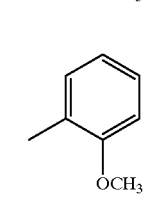 | |
-continued
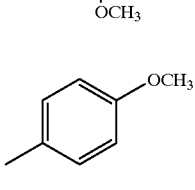
| X₁ | X₅ | R₄₀ | mp °C. |
|---|---|---|---|
| H | H | 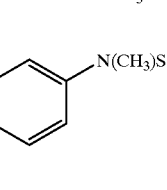 | 208–210 |
| H | H | 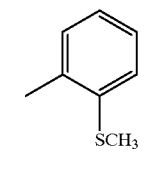 | |
| H | H | 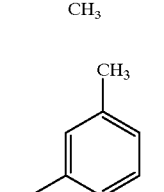 | |
| H | H | 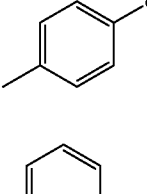 | |
| Br | F | CH₃ | |
| H | F | 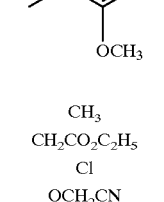 | |
| H | F | CH₃ | |
| H | H | CH₂CO₂C₂H₅ | |
| H | H | Cl | |
| H | H | OCH₂CN | 254–258 |
| H | H | OCH₃ | |
| H | H | OCH(CH₃)₂ | 180–185 |
| H | H | OCH₂CH=CH₂ | 210–212 |
| H | H | OCH₂C≡CH | 212–215 |
| H | H | OCH₂CO₂CH₃ | |

EXAMPLE 3

Preparation of 3-[3-(6-Methoxy-m-tolyl)-1,2-benzisothiazol-5-yl]-1-methyl-6-(trifluoromethyl)-2,4(1H,3H)-pyrimidinedione

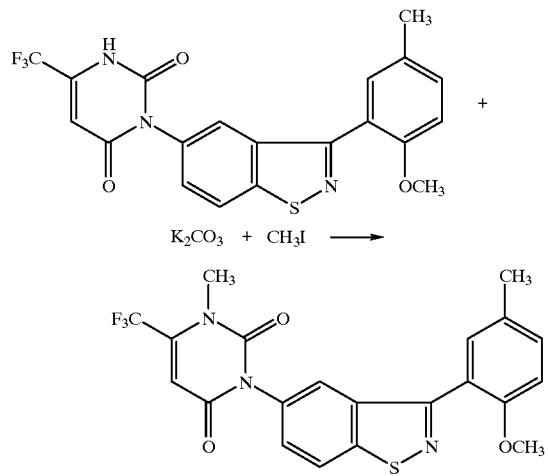

K₂CO₃ + CH₃I ⟶

A mixture of 3-[3-(6-methoxy-m-tolyl)-1,2-benzisothiazol-5-yl]-6-(trifluoromethyl)-2,4(1H,3H)-pyrimidinedione (160 g, 0.369 mol), potassium carbonate (76.6 g, 0.554 mol) and iodomethane (34.5 mL, 0.554 mol) in N,N-dimethylformamide is stirred at room temperature for 4 hours, and poured onto ice. The resultant aqueous mixture is extracted with methylene chloride. The organic extract is diluted with hexanes, washed with water, dried over anhydrous magnesium sulfate, and concentrated in vacuo to obtain the title product as an orange foam (163 g, 98.8%) which is identified by NMR spectral analyses.

Using essentially the same procedure, the following compounds are obtained:

| $X_1$ | $X_5$ | Z | $R_{40}$ | mp °C. |
|---|---|---|---|---|
| H | H | $CH_3$ | H | 223–225 |
| H | H | $CH_3$ | CN | 239–240 |
| H | H | $CH_3$ | $CH_3$ | 244–245 |
| H | H | $CH_3$ | $CH_2OCH_2CO_2CH_3$ | 143–144 |
| H | H | $CH_3$ | $C_2H_5$ | 171–172 |
| H | H | $CH_3$ | 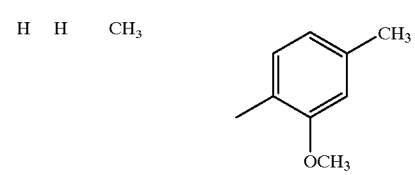 | 198–200 |

-continued

| $X_1$ | $X_5$ | Z | $R_{40}$ | mp °C. |
|---|---|---|---|---|
| H | H | $CH_3$ | 4-ethylphenyl | 170.5–172 |
| H | H | $CH_3$ | 4-methylphenyl | 175.5–180 |
| H | H | $CH_3$ | 2-methoxyphenyl | 173–175 |
| H | H | $CH_3$ | 2,4,5-trimethyl-4-methoxyphenyl | 225–227 |
| H | H | $CH_3$ | 2,3-dimethyl-4-methoxyphenyl | 185–187 |
| H | H | $CH(CH_3)_2$ | 2,5-dimethyl-4-methoxyphenyl | — |
| H | H | $CH_3$ | 2,5-dimethyl-4-methoxyphenyl | — |

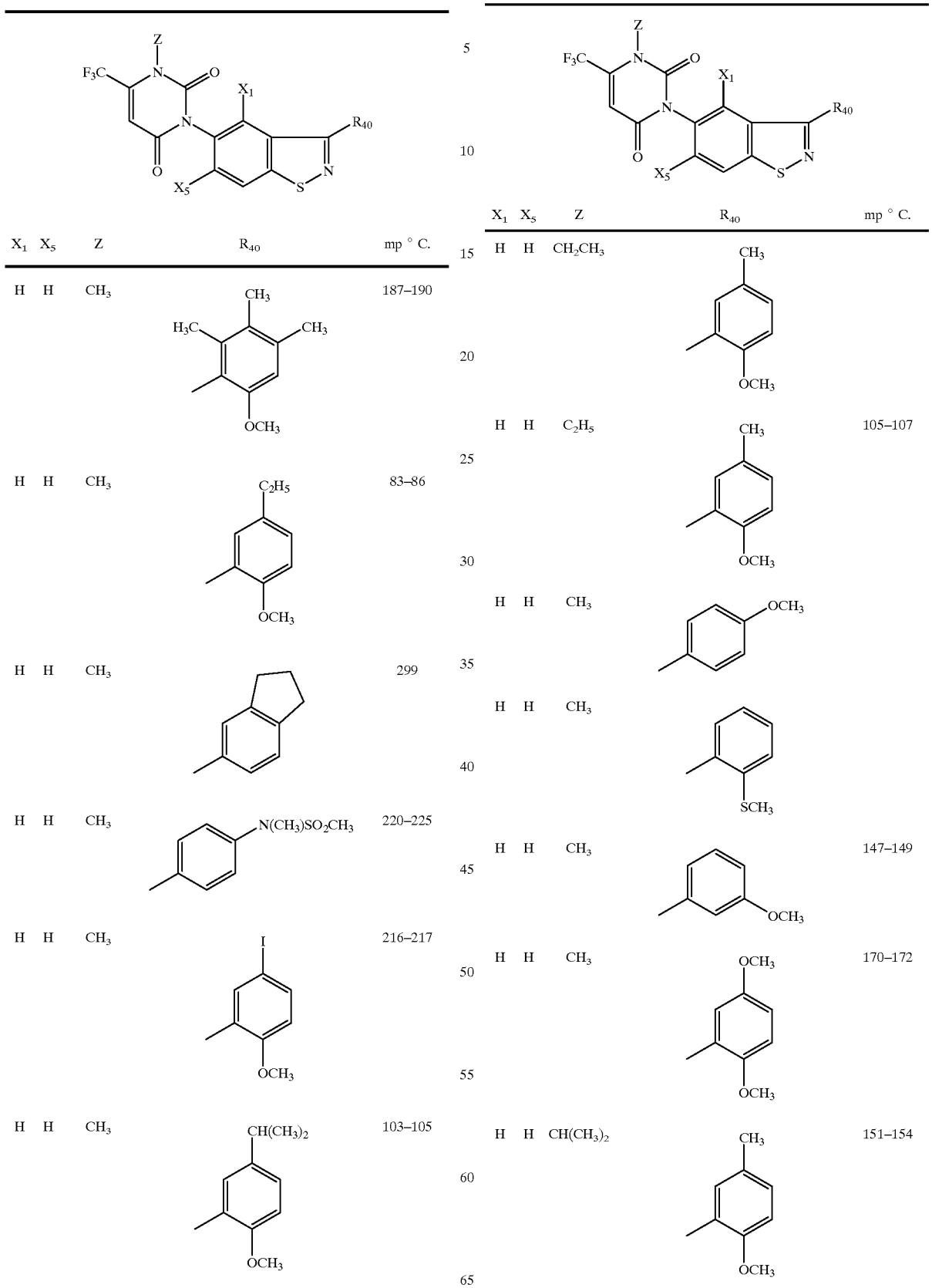

-continued

[Structure: pyrimidinedione fused with benzisothiazole bearing substituents $X_1$, $X_5$, Z, $R_{40}$ with $F_3C$ group]

| $X_1$ | $X_5$ | Z | $R_{40}$ | mp °C. |
|---|---|---|---|---|
| H | H | $CH_3$ | 4-Cl-phenyl | |
| H | H | $CH_3$ | 4-Cl-2,5-dimethyl-methoxyphenyl (Cl, $CH_3$, $OCH_3$ substituted phenyl) | 227–228 |
| H | F | $CH_3$ | $CH_3$ | |
| H | Cl | $CH_3$ | 3,4-dimethyl-methoxyphenyl | |
| Br | F | $CH_3$ | $CH_3$ | 211–213 |
| H | F | $CH_3$ | 3,4-dimethyl-methoxyphenyl | |
| H | H | $CH_3$ | $CH_2CO_2C_2H_5$ | 150–152 |
| H | H | $CH_3$ | Cl | |
| H | H | $CH_3$ | $OCH_2CN$ | 265–266 |
| H | H | $CH_3$ | $OCH_3$ | 198–199 |
| H | H | $CH_3$ | $OCH(CH_3)_2$ | 125–127 |
| H | H | $CH_3$ | $OCH_2CH=CH_2$ | 184–185 |
| H | H | $CH(CH_3)_2$ | 3,4-dimethyl-methoxyphenyl | 151–154 |
| H | H | $CH_3$ | 4-Cl-phenyl | |

-continued

[Structure: pyrimidinedione fused with benzisothiazole bearing substituents $X_1$, $X_5$, Z, $R_{40}$ with $F_3C$ group]

| $X_1$ | $X_5$ | Z | $R_{40}$ | mp °C. |
|---|---|---|---|---|
| H | H | $CH_3$ | 4-Cl-2,5-dimethyl-methoxyphenyl | 227–228 |
| H | F | $CH_3$ | $CH_3$ | |
| H | Cl | $CH_3$ | 3,4-dimethyl-methoxyphenyl | |
| Br | F | $CH_3$ | $CH_3$ | 211–213 |
| H | F | $CH_3$ | 3,4-dimethyl-methoxyphenyl | |
| H | H | $CH_3$ | $CH_2CO_2C_2H_5$ | 150–152 |
| H | H | $CH_3$ | Cl | |
| H | H | $CH_3$ | $OCH_2CN$ | 265–266 |
| H | H | $CH_3$ | $OCH_3$ | 198–199 |
| H | H | $CH_3$ | $OCH(CH_3)_2$ | 125–127 |
| H | H | $CH_3$ | $OCH_2CH=CH_2$ | 184–185 |
| H | H | $CH_3$ | $OCH_2C\equiv CH$ | 201–202.5 |
| H | H | $CH_3$ | $OCH_2CO_2CH_3$ | 181–183 |

EXAMPLE 4

Preparation of 3-[3-(6-Methoxy-m-tolyl)-1,2-benzisoxazol-5-yl]-6-(trifluoromethyl)-2,4(1H,3H)-pyrimidinedione

[Structure: 5-amino-3-(6-methoxy-m-tolyl)-1,2-benzisoxazole] +

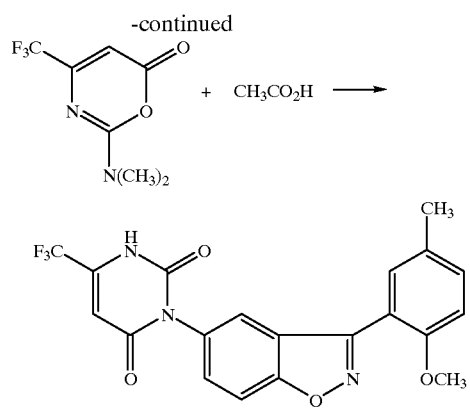

A mixture of 5-amino-3-(6-methoxy-m-tolyl)-1,2-benzisoxazole (8.40 g, 0.033 mol), 2-dimethylamino-4-(trifluoromethyl)-6H-1,3-oxazin-6-one (7.60 g, 0.036 mol), and acetic acid is refluxed for three hours, cooled, poured onto ice, and diluted with water. The resultant aqueous mixture is filtered to obtain a solid. The solid is washed with water and dried to give the title product as a pink solid which is identified by NMR spectral analyses.

Using essentially the same procedure, the following compounds are obtained:

| $X_1$ | $X_5$ | $R_{41}$ | mp ° C. |
|---|---|---|---|
| H | H | 2-methoxy-phenyl | 214–216 |
| H | H | phenyl | |
| Cl | H | 2,5-dimethyl-4-methoxyphenyl | |

| $X_1$ | $X_5$ | $R_{41}$ | mp ° C. |
|---|---|---|---|
| H | F | 2,5-dimethyl-4-methoxyphenyl | |
| H | F | $CH_3$ | 235–237 |
| H | H | $CH_3$ | 283–285 |
| H | H | Cl | |
| H | H | $OCH_2CO_2CH_3$ | 180–182 |
| H | H | $OCH(CH_3)_2$ | 213–215 |
| H | H | $OCH_3$ | 230–235 |
| Cl | F | $CH_3$ | 125–130 |

EXAMPLE 5

Preparation of 3-[3-(6-Methoxy-m-tolyl)-1,2-benzisoxazol-5-yl]-1-methyl-6-(trifluoromethyl)-2,4(1H,3H)-pyrimidinedione

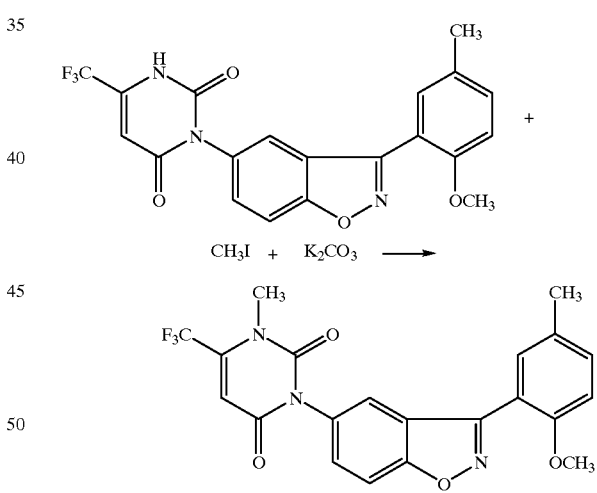

A mixture of 3-[3-(6-methoxy-m-tolyl)-1,2-benzisoxazol-5-yl]-6-(trifluoromethyl)-2,4(1H,3H)-pyrimidinedione (10.5 g, 0.0255 mol) and potassium carbonate (7.04 g, 0.051 mol) in N,N-dimethylformamide is stirred for 15 minutes, treated with methyl iodide (7.24 g, 0.051 mol), stirred overnight, and poured onto ice. The resultant aqueous mixture is extracted with methylene chloride. The organic extracts are combined, washed with water, dried over anhydrous sodium sulfate, and concentrated in vacuo to obtain a brown glass. Dry column chromatography of the glass using silica gel and a hexanes/ethyl acetate solution (3:1) gives the title product as an off-white solid which is identified by NMR spectral analyses.

Using essentially the same procedure, the following compounds are obtained:

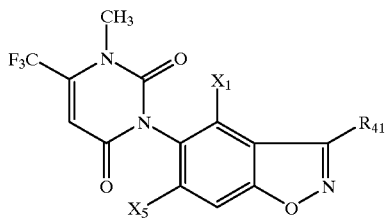

| X₁ | X₅ | R₄₁ | mp ° C. |
|---|---|---|---|
| H | H | (2-methoxyphenyl) | |
| H | H | (4-methylphenyl) | 225–226.5 |
| Cl | H | (3,4-dimethyl-methoxyphenyl) | |
| H | F | (3,4-dimethyl-methoxyphenyl) | |
| H | F | (2-methoxyphenyl) | |
| H | F | CH₃ | 158–159 |
| H | H | CH₃ | 196–198 |
| H | H | Cl | 168.5–170 |
| H | H | OCH₂CO₂CH₃ | 156–157 |
| H | H | OCH(CH₃)₂ | |
| H | H | OCH₃ | 160–161 |
| Cl | F | CH₃ | 154–155 |

EXAMPLE 6

Preparation of Ethyl 5-[3,6-dihydro-3-methyl-2,6-dioxo-4-(trifluoromethyl)-1(2H)-pyrimidinyl]-α,α-dimethyl-1,2-benzisothiazole-3-acetate

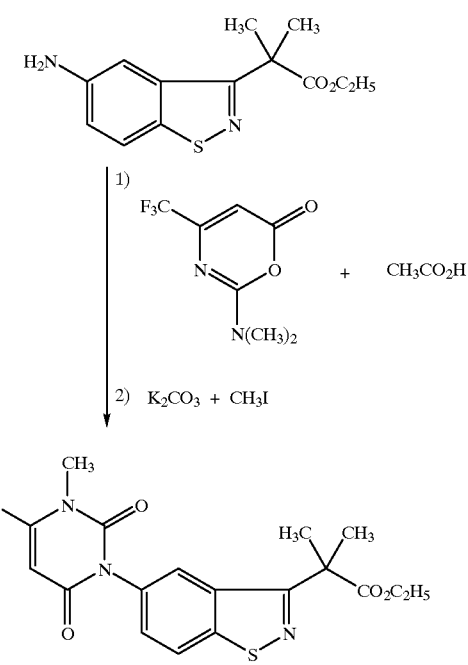

A mixture of ethyl 5-amino-α,α-dimethyl-1,2-benzisothiazole-3-acetate (0.546 g, 2.06 mmol) and 2-dimethylamino-4-(trifluoromethyl)-6H-1,3-oxazin-6-one (0.430 g, 2.06 mmol) in acetic acid is refluxed for 4.5 hours, concentrated in vacuo, and diluted with saturated sodium hydrogen carbonate solution. The resultant aqueous mixture is extracted with methylene chloride. The combined organic extracts are washed with water, dried over anhydrous sodium sulfate, and concentrated in vacuo to obtain a brown foam. A solution of the foam in N,N-dimethylformamide is treated with potassium carbonate (0.312 g, 2.25 mmol), stirred for one hour, treated with iodomethane (0.420 mL, 6.70 mmol), stirred overnight at room temperature, and poured into an ice-water mixture containing 20 mL of concentrated hydrochloric acid. The resultant aqueous mixture is extracted with methylene chloride. The combined organic extracts are washed sequentially with 10% hydrochloric acid, water, saturated sodium hydrogen carbonate solution and water, dried over anhydrous sodium sulfate and concentrated in vacuo to obtain a brown oil. Column chromatography of the oil using silica gel and a 33% ethyl acetate in methylene chloride solution affords a pink foam which is recrystallized from ethanol to give the title product as pink crystals, mp 164–167° C.

EXAMPLE 7
Preparation of 2'-Chloro-2-methoxy-5-methyl-5'-nitrobenzophenone

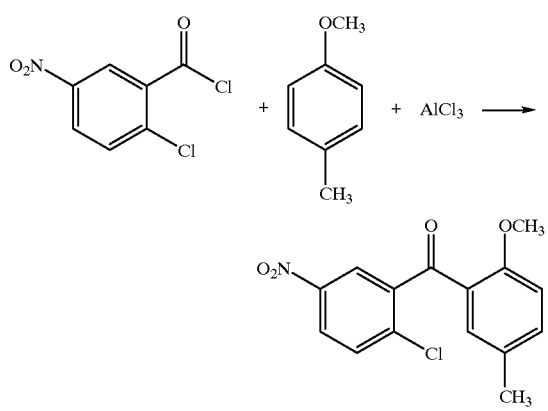

A mixture of aluminum chloride (33.3 g, 25.0 mmol) in methylene chloride is cooled to about 5° C., treated over one hour with p-methylanisole (31.6 g, 25.0 mmol) while maintaining the reaction mixture temperature below 10° C., treated over 20 minutes with a solution of 2-chloro-5-nitrobenzoyl chloride (50.0 g, 22.7 mmol) in methylene chloride while maintaining the reaction mixture temperature below 10° C., warmed to and stirred at room temperature for 60 minutes, and poured onto ice. The resultant aqueous mixture is treated with concentrated hydrochloric acid (50 mL) and extracted with methylene chloride. The organic extract is dried over anhydrous magnesium sulfate and concentrated in vacuo to give a yellow solid. After placing the solid in a Kugelrohr apparatus at 40° C. to remove residual p-methylanisole, the title product is obtained as a beige solid (68.8 g, 99.1%) which is identified by NMR spectral analyses.

Using essentially the same procedure, the following compounds are obtained:

| $X_3$ | $X_5$ | W | $W_1$ | $W_2$ | $W_3$ | $W_4$ | mp ° C. |
|---|---|---|---|---|---|---|---|
| Cl | H | | | | | | |
| Cl | H | H | I | H | H | $OCH_3$ | 115–116.5 |
| Cl | H | H | H | $CH_3$ | H | $OCH_3$ | |
| Cl | H | H | H | $C_2H_5$ | H | H | |
| Cl | H | H | $CH_3$ | $CH_3$ | H | $OCH_3$ | |
| Cl | H | H | H | $OCH_3$ | H | H | 108–112 |
| Cl | H | H | $C_2H_5$ | H | H | $OCH_3$ | 98–99.5 |
| Cl | H | H | H | $OCH_3$ | H | $CH_3$ | 91–92 |
| Cl | H | H | H | $CH_3$ | H | H | 95.5–96.5 |
| Cl | H | H | H | $SCH_3$ | H | H | 127–128 |
| Cl | H | H | H | $CH_3$ | H | $OCH_3$ | 91–92.5 |
| Cl | H | H | H | $C_2H_5$ | H | H | |
| Cl | H | H | H | Cl | H | H | 88.5–90.5 |
| Cl | H | H | H | F | H | H | 68–69.5 |
| Cl | H | H | Cl | H | H | $OCH_3$ | 124–126 |
| Cl | H | H | $OCH_3$ | H | H | $OCH_3$ | 71–73 |
| Cl | H | H | H | $OCH_3$ | H | $OCH_3$ | 98–100 |
| Cl | H | H | $CH_3$ | $CH_3$ | H | $OCH_3$ | 127–129 |
| Cl | H | H | H | Cl | H | $OCH_3$ | 96–99 |
| Cl | H | $CH_3$ | H | $CH_3$ | H | $OCH_3$ | 108.5–110 |
| Cl | H | H | H | H | $CH_3$ | $OCH_3$ | 71–74 |
| Cl | H | H | H | $N(CH_3)SO_2CH_3$ | H | H | |
| Cl | H | H | $CH_3$ | Cl | H | $OCH_3$ | 126–128 |
| Cl | H | H | $CH_3$ | H | $CH_3$ | $OCH_3$ | 110–112 |
| Cl | H | $CH_3$ | $CH_3$ | $CH_3$ | H | $OCH_3$ | 104–106 |
| Cl | H | H | $CH(CH_3)_2$ | H | H | $OCH_3$ | 69–71 |
| Cl | H | H | $CH_3$ | H | H | H | |
| Cl | H | H | H | H | H | CN | |
| Cl | H | H | H | H | H | $OCH_3$ | |
| Cl | H | H | $OCH_3$ | H | H | H | |
| Cl | H | H | F | H | H | $OCH_3$ | |
| Cl | H | H | H | F | H | $OCH_3$ | |
| Cl | H | H | H | H | H | $SCH_3$ | |

-continued

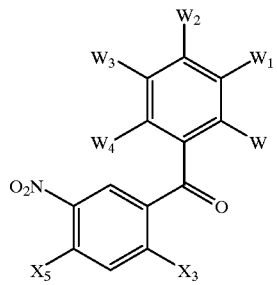

| $X_3$ | $X_5$ | W | $W_1$ | $W_2$ | $W_3$ | $W_4$ | mp °C. |
|---|---|---|---|---|---|---|---|
| Cl | H | H | H | H | H | $CH_3$ | |
| Cl | H | H | H | H | H | F | |
| Cl | H | H | $SCH_3$ | H | H | H | |
| Cl | H | H | H | $OCH_3$ | H | H | |
| Cl | H | H | —$(CH_2)_3$— | | H | $OCH_3$ | |
| Cl | F | H | H | H | H | H | |
| F | F | H | $CH_3$ | H | H | $OCH_3$ | |

EXAMPLE 8

Preparation of 3-(6-Methoxy-m-tolyl)-5-nitro-1,2-benzisothiazole

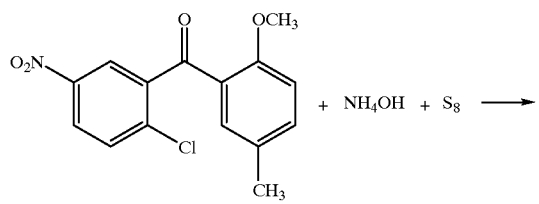

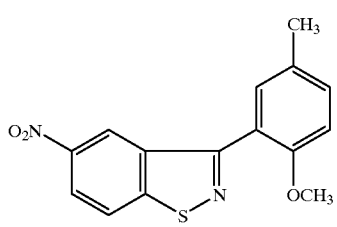

Ammonium hydroxide (350 mL of a 30% solution, 270 mmol) is added to a mixture of 2'-chloro-2-methoxy-5-methyl-5'-nitrobenzophenone (68.7 g, 22.5 mmol) and sulfur (7.57 g, 23.6 mmol) in N,N-dimethylformamide. The resultant reaction mixture is stirred at 80° C. for 19.5 hours, cooled to 40° C., treated with additional ammonium hydroxide (50 mL of a 30% solution), stirred at 80° C. for 25 hours, cooled, and poured onto ice. The resultant aqueous mixture is filtered to obtain the title product as a yellow solid (63.5 g, 93.9%) which is identified by NMR spectral analyses.

Using essentially the same procedure, the following compounds are obtained:

| W | $W_1$ | $W_2$ | $W_3$ | $W_4$ | mp °C. |
|---|---|---|---|---|---|
| H | H | $CH_3$ | H | $OCH_3$ | 201–203 |
| H | $CH_3$ | $CH_3$ | H | $OCH_3$ | 199–200 |
| H | $CH_3$ | H | H | H | 116.5–117.5 |
| H | H | Cl | H | $OCH_3$ | 229–231 |
| H | H | H | $CH_3$ | $OCH_3$ | 134–136 |
| H | H | H | H | CN | 187.5–189 |
| H | H | H | H | $OCH_3$ | 193–198 |
| H | H | $OCH_3$ | H | H | 201–203 |
| H | $OCH_3$ | H | H | H | 174–175 |
| H | F | H | H | $OCH_3$ | 224–226 |
| H | $C_2H_5$ | H | H | $OCH_3$ | 153–154.5 |
| H | H | $CH_3$ | H | H | 188–189 |
| H | H | $N(CH_3)SO_2CH_3$ | H | H | |
| H | $CH_3$ | Cl | H | $OCH_3$ | 230–234 |
| H | I | H | H | $OCH_3$ | |
| H | H | $SCH_3$ | H | H | 177.5–178.5 |
| H | H | $OCH_3$ | H | $CH_3$ | 131–135 |
| H | H | F | H | H | 226–228 |
| H | H | Cl | H | H | 217.5–219 |
| H | H | F | H | $OCH_3$ | 224–225 |
| H | H | H | H | $SCH_3$ | 114.5–115.5 |
| H | H | $CH_3$ | H | $OCH_3$ | 201–203 |
| H | $OCH_3$ | H | H | $OCH_3$ | 195–196 |
| H | H | H | H | $CH_3$ | 145–146 |
| H | H | H | H | F | 181–182 |
| H | H | $OCH_3$ | H | $OCH_3$ | 171–172.5 |
| H | $SCH_3$ | H | H | H | 139–140.5 |
| H | $CH_3$ | H | $CH_3$ | $OCH_3$ | |
| $CH_3$ | $CH_3$ | $CH_3$ | H | $OCH_3$ | |
| H | $CH(CH_3)_2$ | H | H | $OCH_3$ | |
| H | H | $CH_3$ | $CH_3$ | $OCH_3$ | |
| H | —$(CH_2)_3$— | | H | $OCH_3$ | | and

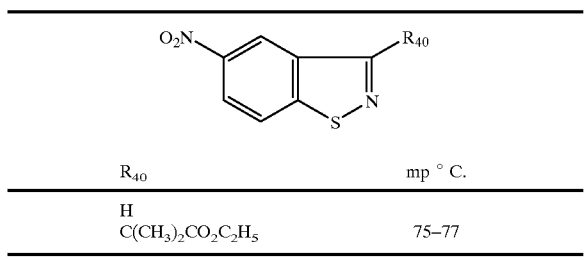

| $R_{40}$ | mp ° C. |
|---|---|
| H | |
| $C(CH_3)_2CO_2C_2H_5$ | 75–77 |

EXAMPLE 9

Preparation of 3-Methyl-5-nitro-1,2-benzisothiazole

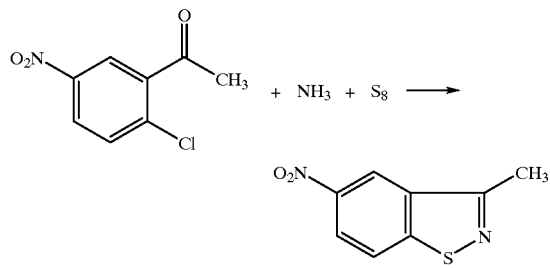

Ammonia (45 g, 2,642 mmol) is bubbled into methanol at −40° C. in a steel bomb. Sulfur (30.5 g, 95.0 mmol) and 2'-chloro-5'-nitroacetophenone (19 g, 95.0 mmol) are then added. The bomb is sealed and heated at about 90° C. overnight. After cooling, the reaction mixture is removed from the bomb and concentrated in vacuo to obtain a residue. The residue is diluted with methylene chloride, passed through a plug of silica gel and concentrated in vacuo to give the title product as an orange solid (12.0 g) which is identified by NMR spectral analyses.

Using essentially the same procedure, the following compounds are obtained:

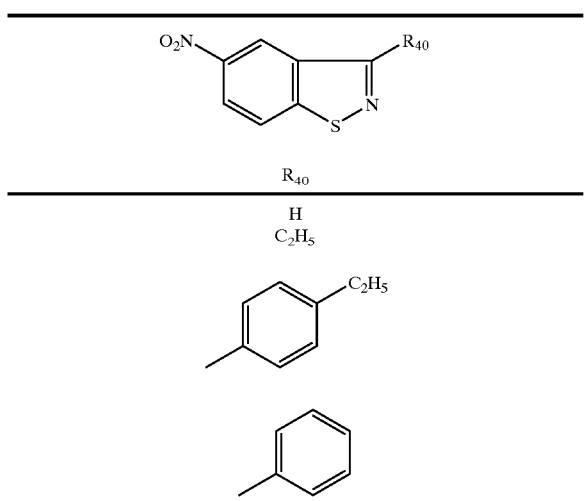

| $R_{40}$ |
|---|
| H |
| $C_2H_5$ |
| (4-ethylphenyl) |
| (4-methylphenyl) |

EXAMPLE 10

Preparation of 5-Amino-3-(6-methoxy-m-tolyl)-1,2-benzisothiazole

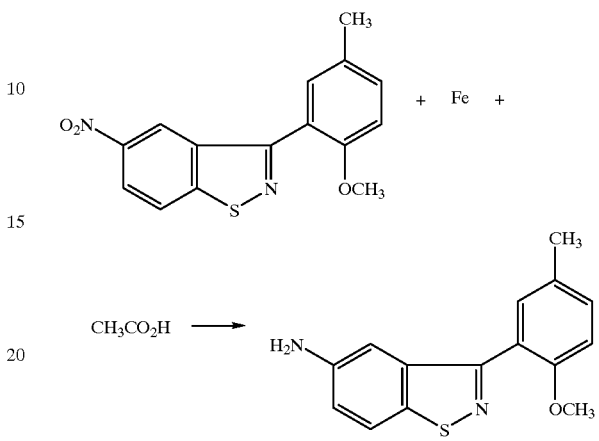

A mixture of 3-(6-methoxy-m-tolyl)-5-nitro-1,2-benzisothiazole (63.0 g, 0.210 mol), 5% acetic acid (1.52 L, 1.21 mol) and ethyl acetate (975 mL) is heated to 65° C., treated portionwise with iron powder (58.6 g, 1.05 mol), stirred at 65° C., and filtered through quartz filter paper. The filtrate phases are separated and the aqueous phase is extracted with ethyl acetate. The organic phase and extracts are combined, washed sequentially with water and brine, dried over anhydrous magnesium sulfate, and concentrated in vacuo to obtain the title product as an orange oil (55.7 g, 98.1%) which is identified by NMR spectral analyses.

Using essentially the same procedure, the following compounds are obtained:

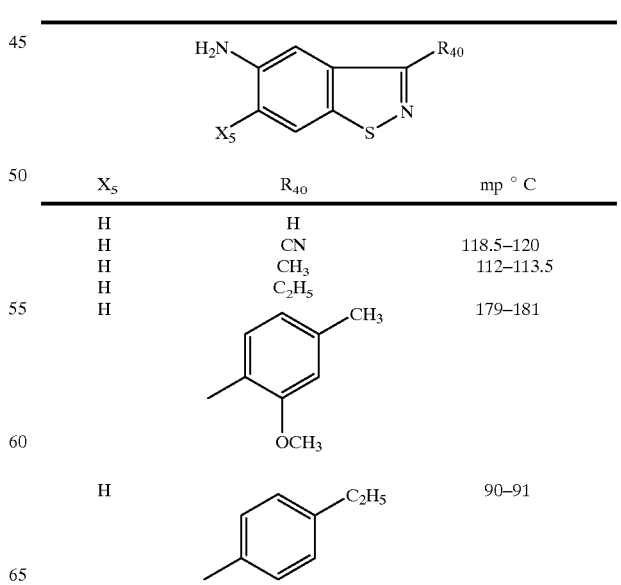

| $X_5$ | $R_{40}$ | mp ° C |
|---|---|---|
| H | H | |
| H | CN | 118.5–120 |
| H | $CH_3$ | 112–113.5 |
| H | $C_2H_5$ | |
| H | (2,5-dimethyl-4-methoxyphenyl) | 179–181 |
| H | (4-ethylphenyl) | 90–91 |

-continued
| $X_5$ | $R_{40}$ | mp °C |
|---|---|---|
| F | 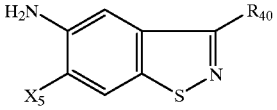 | |
| H | 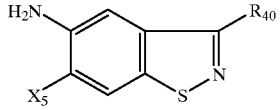 | 130–130.5 |
| H | 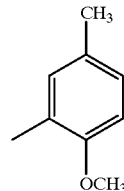 | 152–153 |
| H | 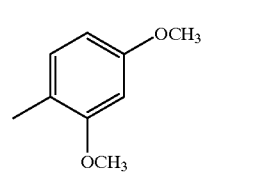 | 121.5–123 |
| H | 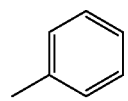 | 108.5–109.5 |
| H | 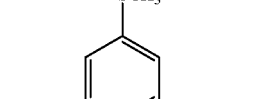 | 158.5–161 |
| H | 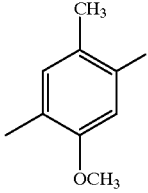 | 101.5–102.5 |
| H | 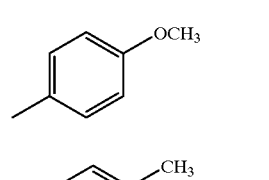 | 104–105 |
-continued
| $X_5$ | $R_{40}$ | mp °C |
|---|---|---|
| H | 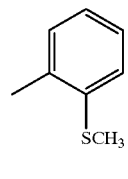 | 191–192.5 |
| H | 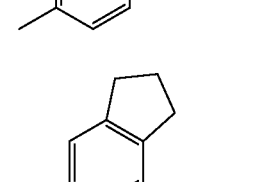 | |
| H | 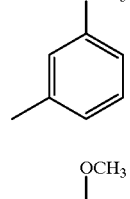 | |
| H | 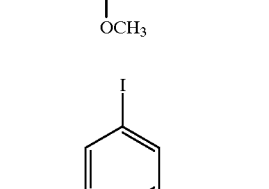 | 128–129 |
| H | 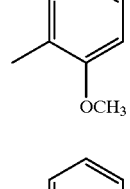 | |
| H | 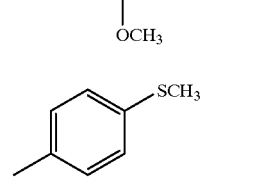 | 64 |
| H | 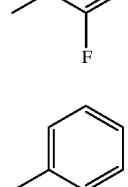 | 108.5–109.5 |
| H | 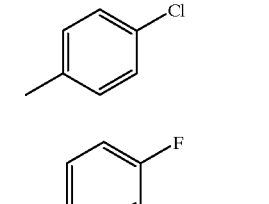 | 133–134 |
| H | 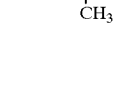 | 114.5–115 |

-continued
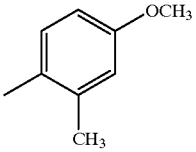
| X₅ | R₄₀ | mp °C |
|---|---|---|
| H | 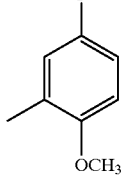 | 152–153.3 |
| H | 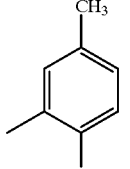 | 146–147 |
| H | 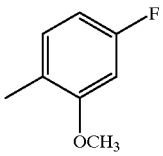 | 60–65 |
| H | 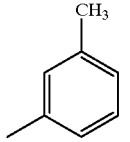 | 143–145 |
| H | 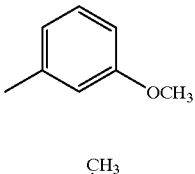 | 100–101 |
| H | 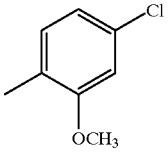 | |
| H | 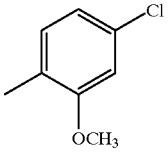 | 125–127 |
-continued
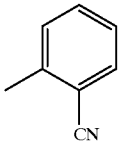
| X₅ | R₄₀ | mp °C |
|---|---|---|
| H | | 172–174 |
| H | 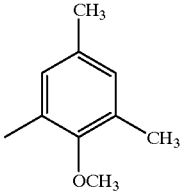 | 146–147 |
| H | 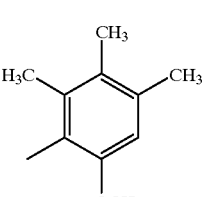 | 161–162 |
| H | 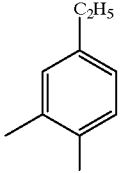 | 173–175 |
| H | | |
| H | 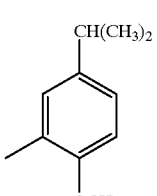 | |

-continued

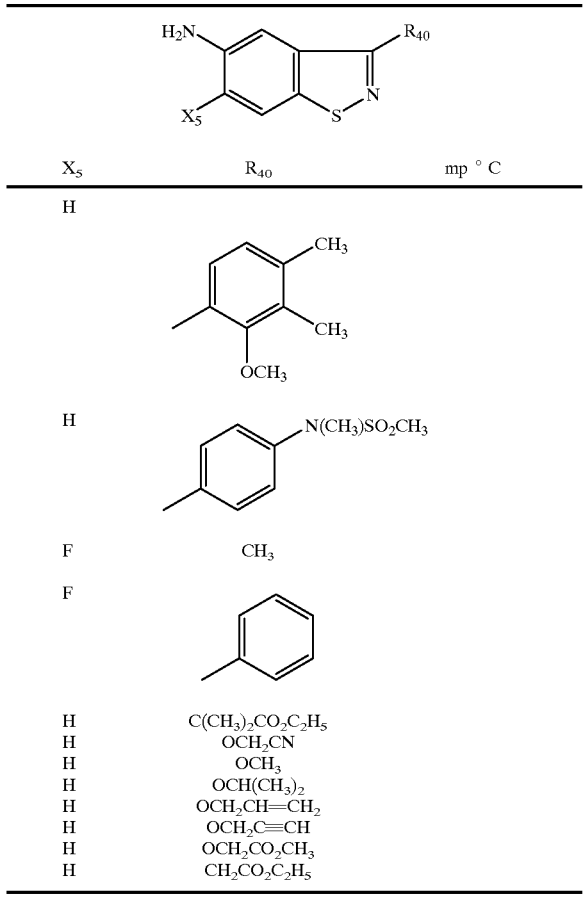

| $X_5$ | $R_{40}$ | mp °C |
|---|---|---|
| H | | |
| H | | |
| F | $CH_3$ | |
| F | | |
| H | $C(CH_3)_2CO_2C_2H_5$ | |
| H | $OCH_2CN$ | |
| H | $OCH_3$ | |
| H | $OCH(CH_3)_2$ | |
| H | $OCH_2CH=CH_2$ | |
| H | $OCH_2C\equiv CH$ | |
| H | $OCH_2CO_2CH_3$ | |
| H | $CH_2CO_2C_2H_5$ | |

EXAMPLE 11

Preparation of 2-chloro-2'-methoxy-5'-methyl-5-nitrobenzophenone, oxime

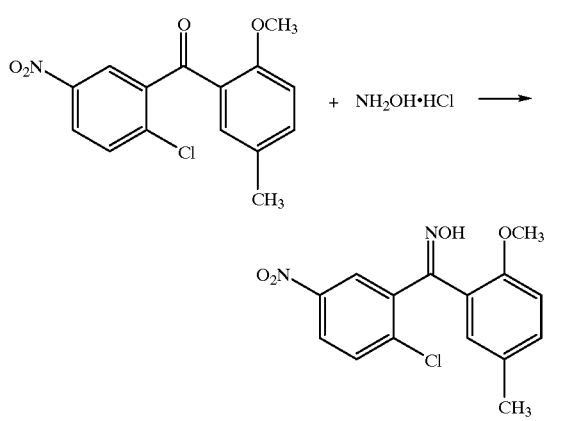

A mixture of 2-chloro-2'-methoxy-5'-methyl-5-nitrobenzophenone (90.0 g, 0.294 mol) in ethanol is treated with a solution of hydroxylamine hydrochloride (102.3 g, 1.47 mol) in water, refluxed overnight, and poured onto ice. The resultant aqueous mixture is filtered to obtain a solid. The solid is washed with water and dried in a hot vacuum oven overnight to give the title product as a white solid (84.2 g) which is identified by $^1H$ NMR spectral analysis.

Using essentially the same procedure, the following compounds are obtained:

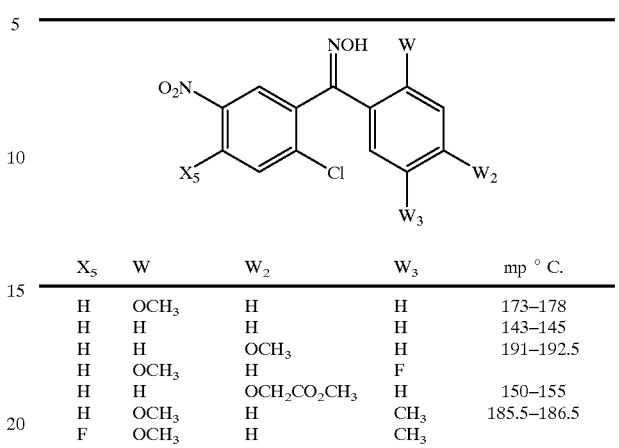

| $X_5$ | W | $W_2$ | $W_3$ | mp °C. |
|---|---|---|---|---|
| H | $OCH_3$ | H | H | 173–178 |
| H | H | H | H | 143–145 |
| H | H | $OCH_3$ | H | 191–192.5 |
| H | $OCH_3$ | H | F | |
| H | H | $OCH_2CO_2CH_3$ | H | 150–155 |
| H | $OCH_3$ | H | $CH_3$ | 185.5–186.5 |
| F | $OCH_3$ | H | $CH_3$ | | and

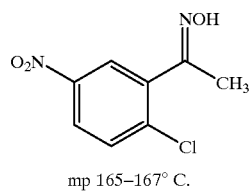

mp 165–167° C.

EXAMPLE 12

Preparation of 3-(6-Methoxy-m-tolyl)-5-nitro-1,2-benzisoxazole

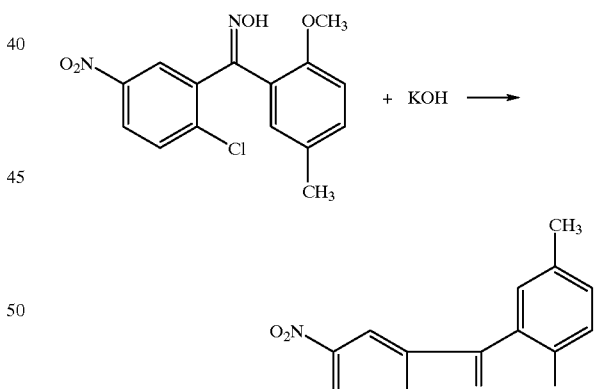

A mixture of 2-chloro-2'-methoxy-5'-methyl-5-nitrobenzophenone, oxime (84.0 g, 0.262 mol) in ethanol is warmed to 65° C., treated with 150 mL of 10% potassium hydroxide solution over 25 minutes, heated to 78° C. over one hour, cooled, and poured onto ice. The resultant aqueous mixture is filtered to obtain a solid. The solid is washed with water, dried, recrystallized from N,N-dimethylformamide, washed sequentially with N,N-dimethyl-formamide and ethanol, and dried in a vacuum oven at 80° C. to give the title product as a solid (mp 225–226° C.) which is identified by $^1H$ NMR spectral analysis.

Using essentially the same procedure, the following compounds are obtained:

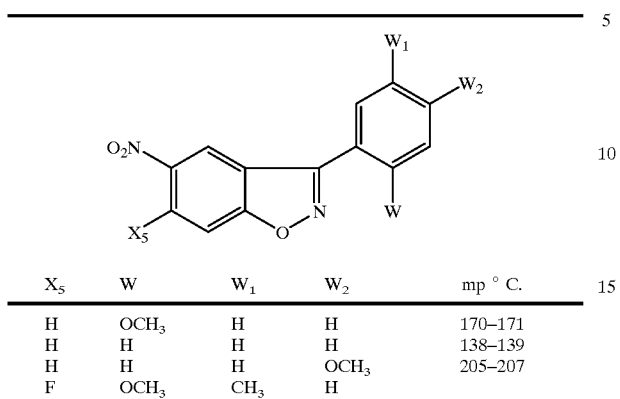

| X₅ | W | W₁ | W₂ | mp ° C. |
|---|---|---|---|---|
| H | OCH₃ | H | H | 170–171 |
| H | H | H | H | 138–139 |
| H | H | H | OCH₃ | 205–207 |
| F | OCH₃ | CH₃ | H | | and

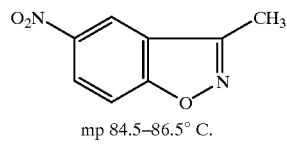

mp 84.5–86.5° C.

EXAMPLE 13

Preparation of m-Fluorophenyl Acetate

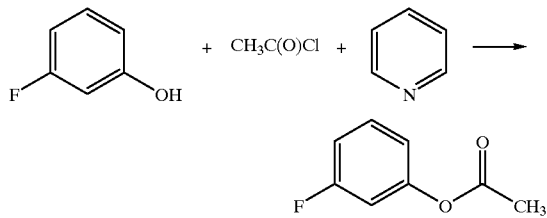

A solution of 3-fluorophenol (100 g, 0.890 mol) in methylene chloride is cooled to 0° C. to 5° C., treated with pyridine (75.0 mL, 0.930 mol), stirred for several minutes, treated dropwise with acetyl chloride (66.0 mL, 0.930 mol) while maintaining the reaction mixture temperature below 17° C., stirred at ice-bath temperature for two hours, warmed to room temperature, and poured into an ice-water mixture. The organic phase is separated, washed with brine, dried over anhydrous magnesium sulfate, and concentrated in vacuo to obtain the title product as a yellow oil which is identified by ¹H NMR spectral analysis.

EXAMPLE 14

Preparation of 4'-Fluoro-2'-hydroxyacetophenone

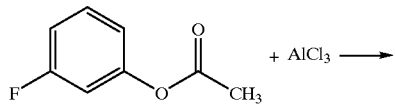

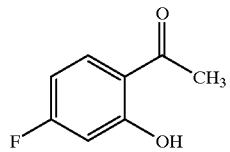

m-Fluorophenyl acetate (123 g, 0.798 mol) is cooled with an ice-bath, treated portionwise with aluminum chloride (150 g, 1.12 mol), stirred at 190° C. for one hour, and cooled to obtain a solid. A mixture of ice, water and hydrochloric acid, and methylene chloride are added to the solid. The resultant mixture is stirred for several minutes, and the phases are separated. The organic phase is washed sequentially with water, saturated sodium hydrogen carbonate solution and brine, dried over anhydrous magnesium sulfate, and concentrated in vacuo to obtain the title product (99.0 g) which is identified by ¹H NMR spectral analysis.

EXAMPLE 15

Preparation of 4'-Fluoro-2'-hydroxyacetophenone, Oxime

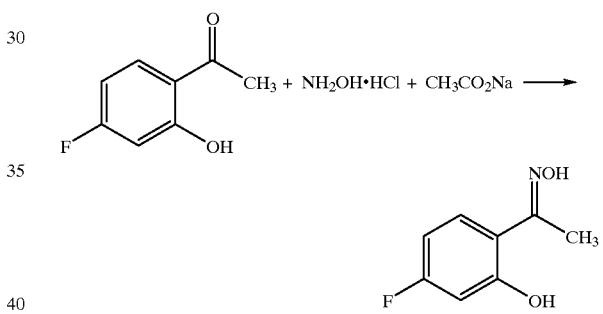

A mixture of 4'-fluoro-2'-hydroxyacetophenone (99.0 g, 0.640 mol), hydroxylamine hydrochloride (89.0 g, 1.28 mol), and sodium acetate (79.0 g, 0.960 mol) in methanol is refluxed for one hour and poured into an ice-water mixture. The resultant aqueous mixture is filtered to obtain a solid. The solid is dissolved in methylene chloride, and the resultant organic solution is dried over anhydrous magnesium sulfate, concentrated in vacuo, diluted with hexanes, and filtered to give the title product as a solid (55.0 g, mp 112–114° C.) which is identified by ¹H NMR spectral analysis.

EXAMPLE 16

Preparation of 6-Fluoro-3-methyl-1,2-benzisoxazole

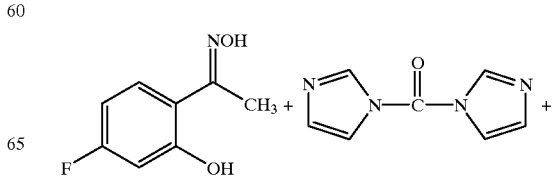

-continued

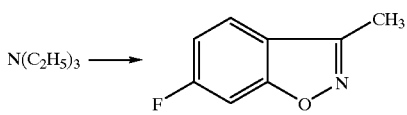

A mixture of 4'-fluoro-2'-hydroxyacetophenone, oxime (47.0 g, 0.278 mol) in tetrahydrofuran is heated to just under reflux, treated with a solution of 1,1'-carbonyldiimidazole (55.0 g, 0.340 mol) and triethylamine (39.0 g, 0.390 mol) in tetrahydrofuran, refluxed for one hour, cooled, concentrated in vacuo, and poured into an ice-water mixture. The resultant aqueous mixture is extracted with ether. The organic extracts are combined, washed sequentially with saturated ammonium chloride solution and brine, dried over anhydrous magnesium sulfate, and concentrated in vacuo to obtain an oil. Column chromatography of the oil using silica gel and a methylene chloride/hexanes solution (1:1) gives the title product as a yellow oil which is identified by $^1$H NMR spectral analysis.

EXAMPLE 17

Preparation of 5-Amino-6-fluoro-3-methyl-1,2-benzisoxazole and 5-Amino-4-chloro-6-fluoro-3-methyl-1,2-benzisoxazole

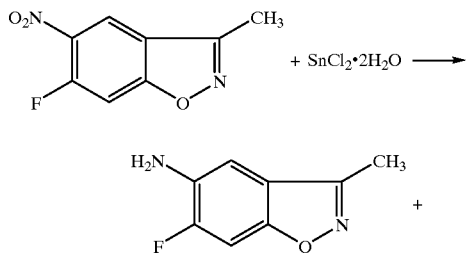

A mixture of 6-fluoro-3-methyl-5-nitro-1,2-benzisoxazole (3.00 g, 0.0153 mol) and acetic acid (85.0 mL) is heated to 40° C., treated with a solution of tin(II) chloride dihydrate (9.70 g, 0.0430 mol) and concentrated hydrochloric acid (45.0 mL), refluxed for 90 minutes, concentrated in vacuo, neutralized with 2N sodium hydroxide solution and filtered to obtain a solid. Column chromatography of the solid using silica gel and methylene chloride gives the title products as solids which are identified by NMR spectral analyses.

Using essentially the same procedure, the following compounds are obtained:

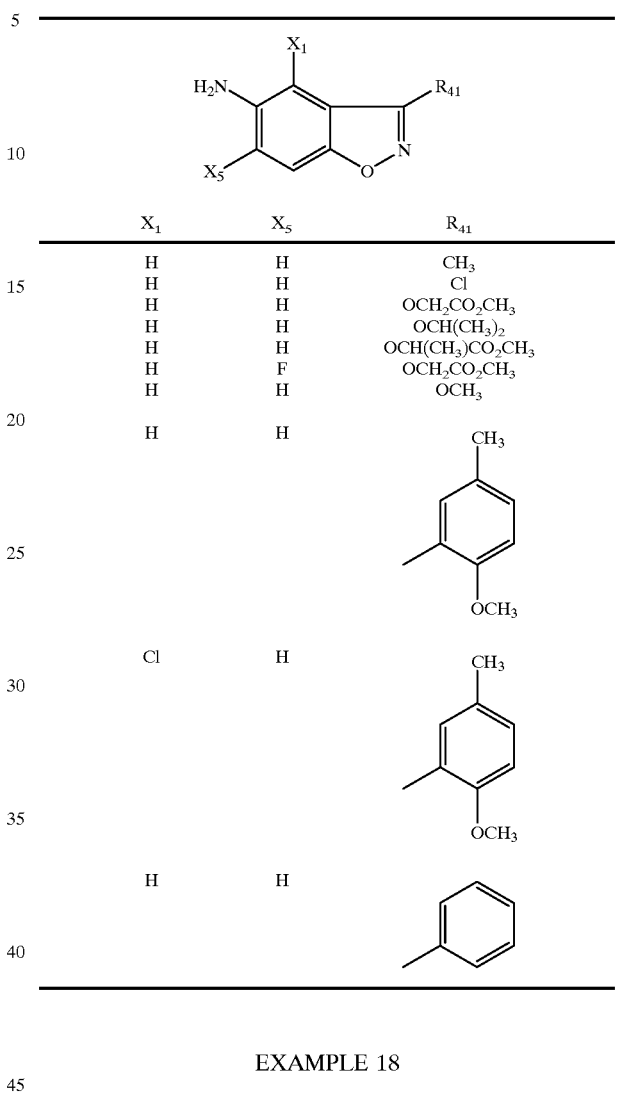

| $X_1$ | $X_5$ | $R_{41}$ |
|---|---|---|
| H | H | $CH_3$ |
| H | H | Cl |
| H | H | $OCH_2CO_2CH_3$ |
| H | H | $OCH(CH_3)_2$ |
| H | H | $OCH(CH_3)CO_2CH_3$ |
| H | F | $OCH_2CO_2CH_3$ |
| H | H | $OCH_3$ |
| H | H | (2,4-dimethyl-methoxyphenyl) |
| Cl | H | (2,4-dimethyl-methoxyphenyl) |
| H | H | (methylphenyl) |

EXAMPLE 18

Preparation of 5-Nitro-1,2-benzisoxazol-3-ol

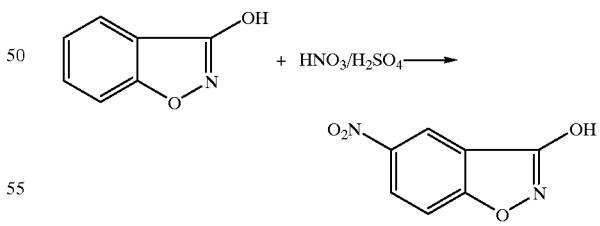

1,2-Benzisoxazol-3-ol (19.7 g, 0.146 mol) is added portionwise to concentrated sulfuric acid. The resultant reaction mixture is treated dropwise with 70% nitric acid (11.3 mL), stirred for 90 minutes, and poured onto ice. The resultant aqueous mixture is filtered to obtain a waxy paste. The paste is recrystallized from a methanol/water mixture to give the title product as a solid which is identified by $^1$H NMR spectral analysis.

Using essentially the same procedure, the following compounds are obtained:

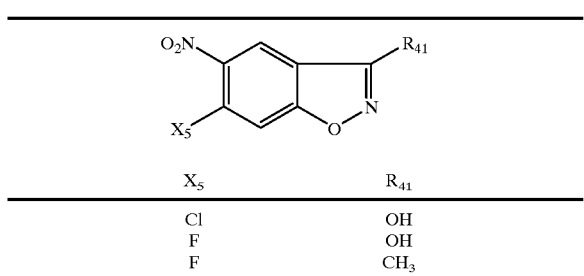

| $X_5$ | $R_{41}$ |
|---|---|
| Cl | OH |
| F | OH |
| F | $CH_3$ |

EXAMPLE 19

Preparation of Methyl [(5-nitro-1,2-benzisoxazol-3-yl)oxy]acetate

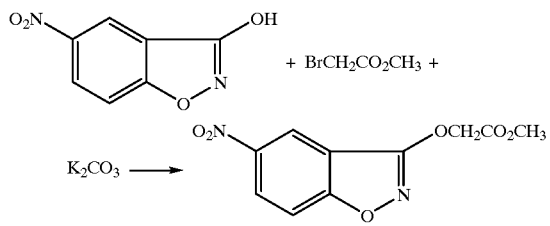

A mixture of 5-nitro-1,2-benzisoxazol-3-ol (3.90 g, 0.0220 mol) and potassium carbonate (4.17 g, 0.0300 mol) in N,N-dimethylformamide is stirred for 30 minutes, treated with methyl bromoacetate (3.96 g, 0.0260 mol), stirred overnight at room temperature, and poured into an acidic ice-water mixture. The resultant aqueous mixture is extracted with ethyl acetate. The organic extracts are combined, washed sequentially with water and brine, dried over anhydrous magnesium sulfate, and concentrated in vacuo to obtain a yellow oil. Column chromatography of the oil using silica gel and a (1:1) to (4:1) methylene chloride/hexanes gradient gives the title product as a white solid (2.80 g, mp 72–73.5° C.) which is identified by NMR spectral analyses.

Using essentially the same procedure, the following compounds are obtained:

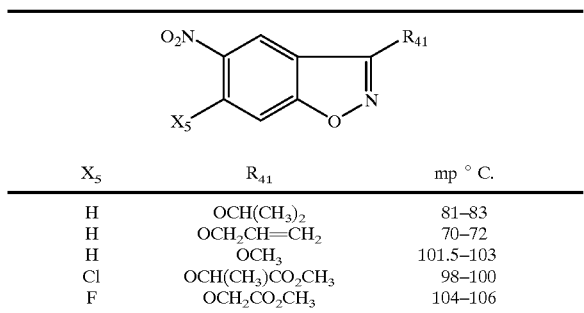

| $X_5$ | $R_{41}$ | mp ° C. |
|---|---|---|
| H | $OCH(CH_3)_2$ | 81–83 |
| H | $OCH_2CH=CH_2$ | 70–72 |
| H | $OCH_3$ | 101.5–103 |
| Cl | $OCH(CH_3)CO_2CH_3$ | 98–100 |
| F | $OCH_2CO_2CH_3$ | 104–106 |

EXAMPLE 20

Preparation of 3-Chloro-5-nitro-1,2-benzisoxazole

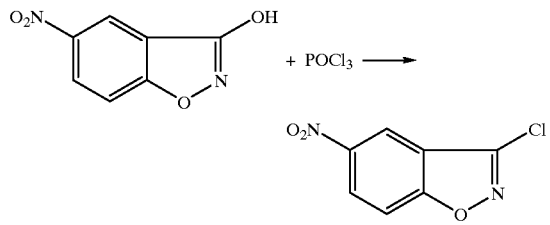

A mixture of 5-nitro-1,2-benzisoxazol-3-ol (4.00 g, 0.0220 mol) and phosphorus oxychloride (40.0 mL, 65.8 g, 0.429 mol) is placed in a glass bomb, heated at 150–155° C. for two hours, cooled overnight, concentrated in vacuo, diluted with methylene chloride, and brought to about pH 8 with sodium hydrogen carbonate solution. The phases are separated. The organic phase is washed sequentially with water and brine, dried over anhydrous magnesium sulfate, and concentrated in vacuo to obtain a residue. Column chromatography of the residue using silica gel and a methylene chloride/hexanes solution (1:1) gives the title product as an amber oil which is identified by NMR spectral analysis.

EXAMPLE 21

Preparation of 2-Chloro-2'-methoxy-5-nitrobenzophenone

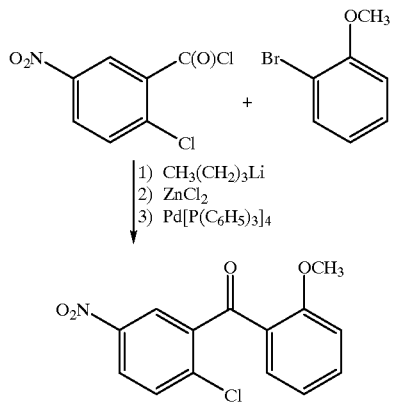

A solution of 2-bromoanisole (27.9 g, 145 mmol) in diethyl ether is cooled to −70° C., treated with butyllithium (64.0 mL, 160 mmol), stirred at −70° C. for one hour, treated with 0.5 M zinc chloride in tetrahydrofuran solution (320 mL, 160 mmol), stirred for one hour at −70° C., warmed to about 0° C., and concentrated in vacuo to obtain a yellow-green oil. A solution of the oil in tetrahydrofuran is treated sequentially with tetrakis(triphenylphosphine)palladium(0) (5.00 g, 4.35 mmol) and a solution of 2-chloro-5-nitrobenzoyl chloride (35.0 g, 159 mmol) in tetrahydrofuran, stirred for three days, and poured into 10% hydrochloric acid. The resultant aqueous mixture is extracted with methylene chloride. The organic extracts are combined, washed sequentially with water and brine, dried over anhydrous magnesium sulfate, and concentrated in vacuo to obtain a semi-solid. The solid is triturated with diethyl ether to give the title product as a yellow solid which is identified by NMR spectral analyses.

Using essentially the same procedure, the following compounds are obtained:

| W₁ | W₂ | W₃ | W₄ | mp °C. |
|---|---|---|---|---|
| H | Cl | H | OCH₃ | 96–99 |
| H | H | CH₃ | OCH₃ | 71–74 |
| F | H | H | OCH₃ | |
| Cl | H | H | OCH₃ | 124–126 |
| OCH₃ | H | H | OCH₃ | 71–73 |
| H | OCH₃ | H | OCH₃ | 98–100 |
| H | F | H | OCH₃ | |
| H | H | CH₃ | H | 65–66.5 |
| H | H | SCH₃ | H | 87–88 |
| H | H | H | F | 118–120 |
| H | H | H | CH₃ | 78–79.5 |
| H | H | H | SCH₃ | 123–124.5 |
| H | F | H | H | |
| H | H | OCH₃ | H | |
| H | H | H | OCH₃ | |
| H | CH₃ | CH₃ | OCH₃ | |

EXAMPLE 22

Preparation of 2-Chloro-2'-methoxy-5-nitrobenzhydrol

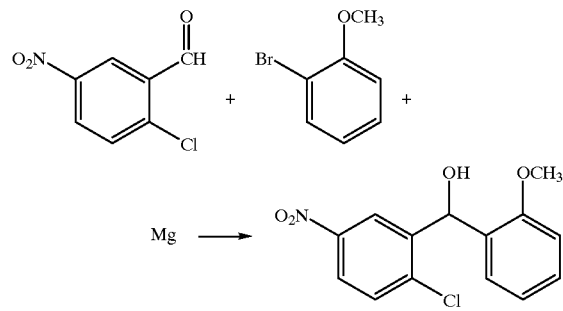

A solution of 2-bromoanisole (50.0 g, 0.267 mol) in ether is added portionwise to a mixture of magnesium (7.10 g, 0.293 mol) in ether. After the addition is complete, the reaction mixture is heated at reflux for one hour, diluted with ether, cooled to 0° C., treated with a solution of 2-chloro-5-nitrobenzaldehyde (39.0 g, 0.210 mol) in tetrahydrofuran, warmed to room temperature, and diluted with an ice-water mixture. After acidifying the aqueous mixture with hydrochloric acid (pH 2—pH 3), the organic phase is separated and the aqueous phase is extracted with ether. The organic extracts are combined, washed sequentially with 10% sodium hydrogen carbonate solution and brine, dried over anhydrous sodium sulfate, and concentrated in vacuo to give the title product as a brown gum.

Using essentially the same procedure, the following compounds are obtained:

| W | W₃ | W₄ |
|---|---|---|
| OCH₃ | H | OCH₃ |
| CH₃ | H | OCH₃ |
| F | H | OCH₃ |
| H | OCH₃ | H |

EXAMPLE 23

Preparation of 2-Chloro-2'-methoxy-5-nitrobenzophenone

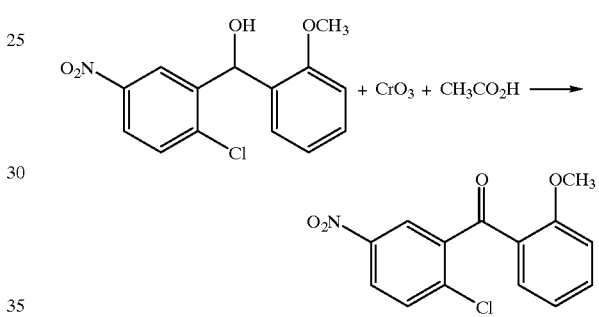

A solution of chromium(VI) oxide (91.0 g, 0.919 mol) in a water/acetic acid solution (1:4) is added portionwise to 2-chloro-2'-methoxy-5-nitrobenzhydrol (64.2 g, 0.219 mol) while maintaining the reaction mixture temperature at 25° C. to 35° C. The reaction mixture is then stirred at 25° C. to 35° C. for one hour, cooled, diluted with water, and concentrated in vacuo to obtain a residue. The residue is diluted with water, and extracted with methylene chloride. The organic extracts are combined, dried over anhydrous sodium sulfate, mixed with silica gel (10 g), and filtered. The filtrate is concentrated in vacuo to obtain an oil. A solution of the oil in a methanol/water solution is decolorized with charcoal and concentrated in vacuo to yield a residue. Column chromatography of the residue using silica gel and methylene chloride/hexanes solutions gives the title product as a white solid.

Using essentially the same procedure, the following compounds are obtained:

| $W_1$ | $W_3$ | $W_4$ | mp ° C. |
|---|---|---|---|
| OCH$_3$ | H | OCH$_3$ | |
| CH$_3$ | H | OCH$_3$ | 109–111 |
| F | H | OCH$_3$ | 94–95 |
| H | OCH$_3$ | H | 79–81 |

EXAMPLE 24

Preparation of 2-Chloro-4-fluoro-5-nitrobenzoyl Chloride

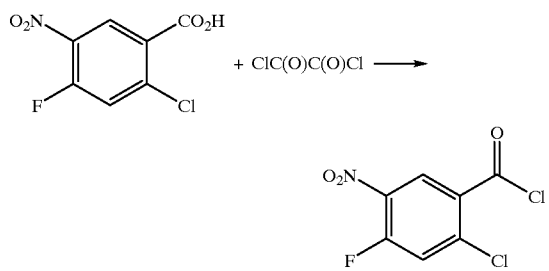

A mixture of 2-chloro-4-fluoro-5-nitrobenzoic acid (50.0 g, 0.228 mol) and N,N-dimethylformamide (5 drops) in 1,2-dichloroethane is treated dropwise with oxalyl chloride (30.8 mL, 0.353 mol), refluxed for 3 hours, cooled, and concentrated in vacuo to obtain the title product as an orange solid which is identified by NMR spectral analyses.

EXAMPLE 25

Preparation of 2'-Chloro-4'-fluoro-5'-nitroacetophenone

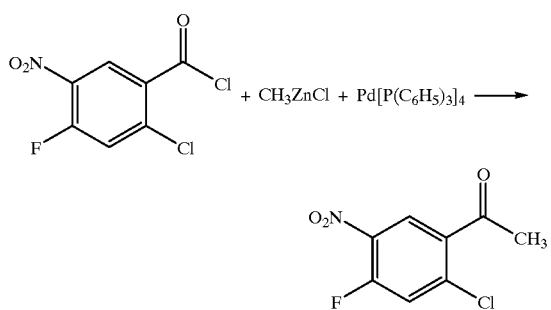

A 2 M solution of methylzinc chloride in tetrahydrofuran (5.00 mL, 10.1 mmol) is treated dropwise with a solution of 2-chloro-4-fluoro-5-nitrobenzoyl chloride (2.00 g, 8.40 mmol) in tetrahydrofuran, treated with tetrakis(triphenylphosphine)palladium(0) (0.400 g, 0.350 mmol), stirred at room temperature for one hour, and poured into 3 N hydrochloric acid. The resultant aqueous mixture is extracted with ethyl acetate. The organic extracts are combined, washed sequentially with water and saturated sodium hydrogen carbonate solution, dried over anhydrous magnesium sulfate, and concentrated in vacuo to obtain a dark liquid. Flash column chromatography of the liquid using silica gel and a methylene chloride in hexanes solution (6:4) gives the title product as an off-white solid (mp 66–68° C.) which is identified by NMR spectral analyses.

EXAMPLE 26

Preparation of 6-Amino-3-methyl-5-nitro-1,2-benzisothiazole

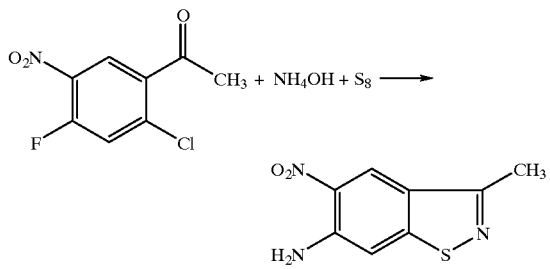

A mixture of 2'-chloro-4'-fluoro-5'-nitroacetophenone (12.0 g, 0.0552 mol), sulfur (1.77 g, 0.0552 mol), 30% ammonium hydroxide solution (100 mL, 0.856 mol), and methanol is placed in a steel bomb, heated at 85° C. overnight, cooled, treated with additional sulfur (0.270 g) and 30% ammonium hydroxide solution (50 mL), heated at 85° C. overnight, cooled, filtered to remove solids, and extracted with ethyl acetate. The organic extracts are combined, washed sequentially with water and brine, dried over anhydrous magnesium sulfate, and concentrated in vacuo to obtain a solid. Flash column chromatography of the solid using silica gel, and 0%, 1% and 2% diethyl ether in methylene chloride solutions gives the title product as an orange solid (4.19 g, mp 189–191° C.) which is identified by NMR spectral analyses.

Using essentially the same procedure, the following compound is obtained:

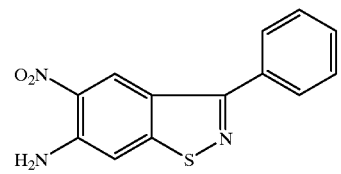

EXAMPLE 27

Preparation of 6-Chloro-3-methyl-5-nitro-1,2-benzisothiazole

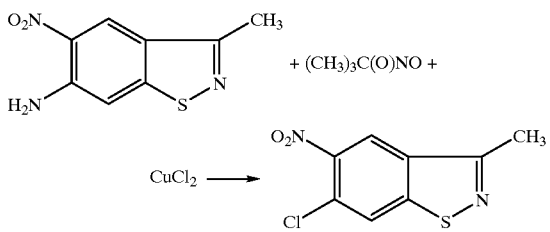

A mixture of tert-butyl nitrite (3.30 mL, 0.0278 mol) and copper(II) chloride (2.98 g, 0.0222 mol) in acetonitrile is heated to 65° C., treated portionwise with 6-amino-3-methyl-5-nitro-1,2-benzisothiazole (3.88 g, 0.0185 mol), stirred at 65° C., cooled to room temperature, and poured into 20% hydrochloric acid. The resultant aqueous mixture is extracted with ethyl acetate. The organic extracts are combined, washed with 20% hydrochloric acid, dried over anhydrous magnesium sulfate, and concentrated in vacuo to obtain a solid. Flash column chromatography of the solid using silica gel and methylene chloride/hexanes solutions (1:1 and 3:1) gives the title product as a pale, yellow solid (2.54 g, mp 156–158° C.) which is identified by NMR spectral analyses.

Using essentially the same procedure, the following compound is obtained:

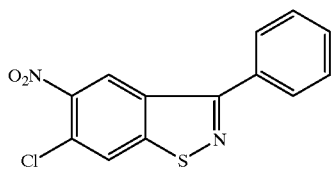

EXAMPLE 28

Preparation of 6-Fluoro-3-methyl-5-nitro-1,2-benzisothiazole

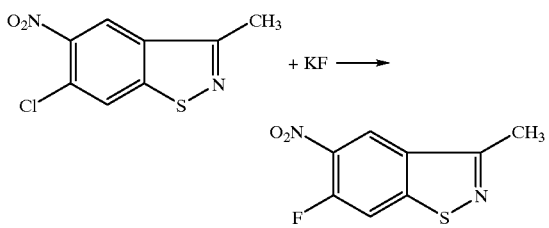

A mixture of 6-chloro-3-methyl-5-nitro-1,2-benzisothiazole (2.25 g, 9.80 mmol), potassium fluoride (2.85 g, 49.0 mmol), and 18-crown-6 (1.50 g, 5.70 mmol) in acetonitrile is heated in a sealed tube for 29 days, filtered to remove solids, and partially concentrated in vacuo to obtain a liquid. The liquid is diluted with ethyl acetate, washed sequentially with water and brine, dried over anhydrous magnesium sulfate, and concentrated in vacuo to obtain a dark, brown solid. Flash column chromatography of the solid using silica gel and a 10% to 50% ethyl acetate in hexanes gradient gives a yellow solid containing two components. Flash column chromatography of the yellow solid using silica gel and a 50% to 70% methylene chloride in hexanes gradient gives the title product as a pale, yellow solid (0.870 g, mp 118–119° C.) which is identified by NMR spectral analyses.

Using essentially the same procedure, the following compound is obtained:

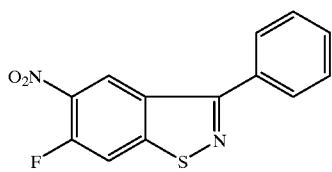

EXAMPLE 29

Preparation of 2,2'-Dithiobis[5-nitrobenzoic acid]

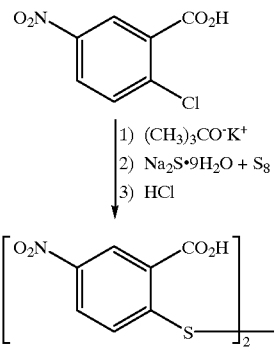

A mixture of 2-chloro-5-nitrobenzoic acid (100 g, 0.496 mol) in ethanol is treated portionwise with potassium tert-butoxide (55.5 g, 0.495 mol), diluted with additional ethanol, heated to reflux, treated portionwise with a solution prepared from sodium sulfide nonahydrate (60.0 g, 0.249 mol), sulfur (8.80 g, 0.274 mol) and water, refluxed for two hours, cooled to room temperature, and treated with concentrated hydrochloric acid. The resultant acidic mixture is stirred for one hour and filtered to obtain a solid. The solid is washed with water and air-dried to give the title product as a yellow powder which is identified by NMR spectral analysis.

EXAMPLE 30

Preparation of 5-Nitro-1,2-benzisothiazol-3(2H)-one

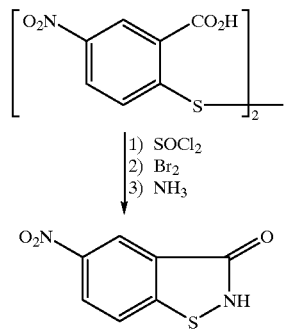

A mixture of 2,2'-dithiobis[5-nitrobenzoic acid] (44.6 g, 0.113 mol) and thionyl chloride (49.0 mL, 0.670 mol) in methylene chloride is treated with N,N-dimethylformamide (0.800 mL), refluxed overnight, concentrated in vacuo, and diluted with 1,2-dichloroethane. The resultant organic solution is treated with bromine (22.5 mL, 0.436 mol), stirred at room temperature for 20 minutes, refluxed for 3.5 hours, and concentrated in vacuo to obtain a residue. A solution of the residue in 1,2-dichloroethane is cooled with an ice-water bath, treated with concentrated ammonia (112 mL) over 15 minutes, stirred at room temperature for 16 hours, cooled with an ice-water bath, and treated with concentrated hydrochloric acid. The resultant aqueous mixture is stirred at room temperature for one hour and filtered to obtain a solid. The solid is washed with water and air-dried to give the title product as a yellow solid which is identified by NMR spectral analysis.

EXAMPLE 31

Preparation of 3-Chloro-5-nitro-1,2-benzisothiazole

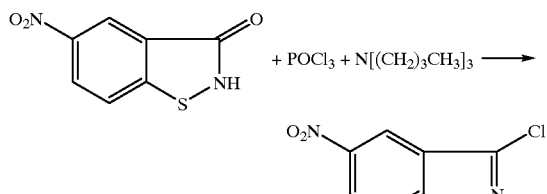

A mixture of 5-nitro-1,2-benzisothiazol-3(2H)-one (10.0 g, 0.0510 mol), phosphorus oxychloride (40.0 mL, 0.429 mol) and tributylamine (12.0 mL, 0.050 mol) is heated at 103–115° C. for six hours, stirred at room temperature overnight, and poured into an ice-water mixture. The resultant aqueous mixture is extracted with methylene chloride. The combined organic extracts are washed sequentially with water and saturated sodium hydrogen carbonate solution, dried over anhydrous sodium sulfate, and concentrated in vacuo to obtain a gum. Column chromatography of the gum using silica gel and methylene chloride gives the title product as an orange-yellow solid which is identified by NMR spectral analysis.

EXAMPLE 32

Preparation of Ethyl α-cyano-5-nitro-1,2-benzisothiazole-3-acetate

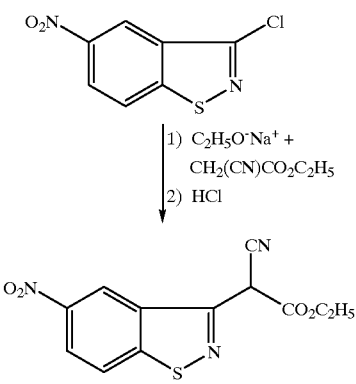

A sodium ethoxide solution (previously prepared from ethanol and sodium (1.00 g, 0.0430 mol)) is cooled with an ice-acetone bath, treated portionwise with ethyl cyanoacetate (4.51 g, 0.0398 mol), stirred at room temperature for 30 minutes, treated with 3-chloro-5-nitro-1,2-benzisothiazole (4.27 g, 0.0199 mol), stirred at room temperature overnight, cooled to 0° C., and treated dropwise with 10% hydrochloric acid (15.0 mL). The resultant aqueous mixture is stirred at room temperature for one hour and filtered to obtain a solid. The solid is washed with ethanol and air-dried to give the title product as a yellow solid which is identified by NMR spectral analysis.

EXAMPLE 33

Preparation of Ethyl 5-nitro-1,2-benzisothiazole-3-acetate

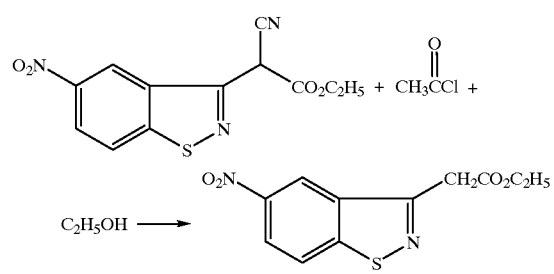

Ethyl α-cyano-5-nitro-1,2-benzisothiazole-3-acetate (6.67 g, 0.0229 mol) is added to a solution of acetyl chloride (67.0 mL) in ethanol. The reaction mixture is refluxed overnight, cooled, and filtered to remove solids. The resultant filtrate is concentrated in vacuo to obtain a brown semi-solid. A mixture of the semi-solid in diethyl ether is stirred for two hours and filtered to obtain a solid. The solid is washed with diethyl ether and air-dried to give the title product as yellow crystals (1.04 g, mp 91–92° C.).

EXAMPLE 34

Preparation of 5-Nitro-1,2-benzisothiazole-3-acetonitrile

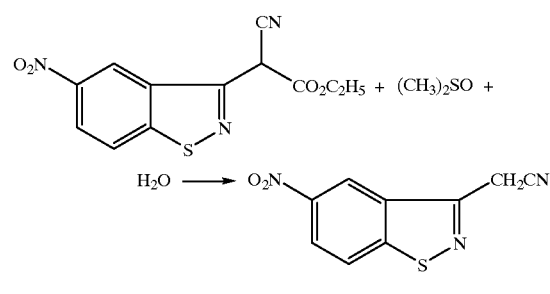

A mixture of ethyl 5-nitro-1,2-benzisothiazole-3-acetate (5.00 g, 17.2 mmol), water (1.00 mL), and methyl sulfoxide (35.0 mL) is stirred at 107° C. for 24 hours, stirred at room temperature for two days, and poured into an ice-water mixture. The resultant aqueous mixture is stirred for two hours and filtered to obtain a solid. The solid is washed with water and air-dried to give the title product as a tan solid.

EXAMPLE 35

Preparation of α,α-Dimethyl-5-nitro-1,2-benzisothiazole-3-acetonitrile

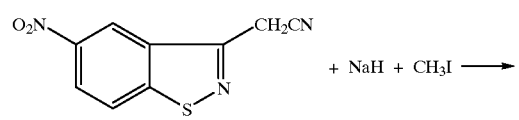

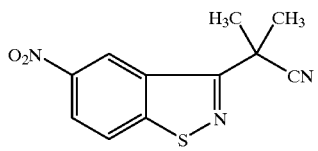

A mixture of 5-nitro-1,2-benzisothiazole-3-acetonitrile (1.29 g, 5.89 mmol) in N,N-dimethylformamide is cooled to −9° C., treated with sodium hydride (1.00 g of a 60% dispersion in oil), stirred at −3° C. for 20 minutes, treated with iodomethane (5.00 mL), stirred at room temperature for four hours, and poured onto ice. The resultant aqueous mixture is treated with 10% hydrochloric acid and extracted with methylene chloride. The combined organic extracts are washed sequentially with water, saturated sodium hydrogen carbonate solution and water, dried over anhydrous sodium sulfate, and concentrated in vacuo to obtain a solid. column chromatography of the solid using silica gel and methylene chloride gives the title product as a yellow solid which is identified by NMR spectral analysis.

EXAMPLE 36

Preparation of Ethyl α,α-dimethyl-5-nitro-1,2-benzisothiazole-3-acetate

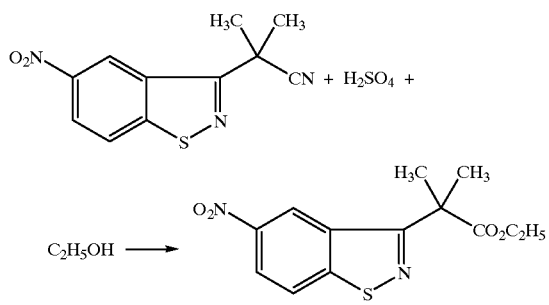

A mixture of α,α-dimethyl-5-nitro-1,2-benzisothiazole-3 3-acetonitrile (0.913 g, 3.69 mmol), water (0.450 mL), concentrated sulfuric acid (4.55 mL) and ethanol (9.10 mL) is refluxed for one hour, cooled, and poured onto ice. The resultant aqueous mixture is neutralized with saturated sodium bicarbonate solution and extracted with methylene chloride. The organic extract is washed with water, dried over anhydrous sodium sulfate, and concentrated in vacuo to obtain a solid. Column chromatography of the solid using silica gel and methylene chloride gives the title product as pale yellow crystals.

EXAMPLE 37

Preparation of 5-Amino-3-chloro-1,2-benzisothiazole

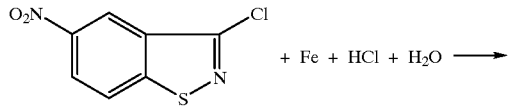

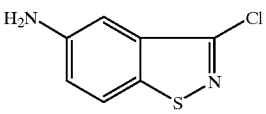

A solution of 3-chloro-5-nitro-1,2-benzisothiazole (2.00 g) in toluene is treated with iron powder (8.40 g, 325 mesh) and concentrated hydrochloric acid (8 drops), heated to reflux, treated dropwise with water (8.00 mL), refluxed for 35 minutes, cooled to room temperature, and filtered through diatomaceous earth. The resultant filtrate is concentrated in vacuo to obtain a residue. Flash column chromatography of the residue using silica gel and an ethyl acetate/hexanes solution (1:1) gives the title product.

EXAMPLE 38

Preparation of [(5-Nitro-1,2-benzisothiazol-3-yl)-oxy]acetonitrile

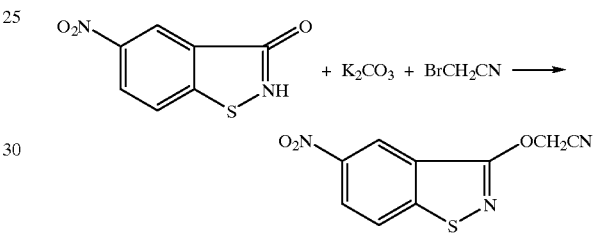

A mixture of 5-nitro-1,2-benzisothiazol-3(2H)-one (17.5 g, 89.2 mmol) in N,N-dimethylformamide is treated with potassium carbonate (18.5 g, 134 mmol), stirred at room temperature for 30 minutes, treated with bromoacetonitrile (16.0 g, 133 mmol), stirred at room temperature overnight, and poured onto ice. The resultant aqueous mixture is acidified to pH 3 with hydrochloric acid and extracted with ethyl acetate. The combined organic extracts are washed sequentially with water and brine, dried over anhydrous magnesium sulfate, and concentrated in vacuo to obtain a solid. Column chromatography of the solid using silica gel and methylene chloride gives the title product as a yellow solid (15.0 g, mp 123–124.5° C.).

Using essentially the same procedure, the following compounds are obtained:

| $R_{40}$ | mp ° C. |
|---|---|
| $OCH_3$ | 108–109 |
| $OCH(CH_3)_2$ | |
| $OCH_2CH{=}CH_2$ | |
| $OCH_2C{\equiv}CH$ | 115–117 |
| $OCH_2CO_2CH_3$ | |

EXAMPLE 39

Preparation of 3-Chloro-5-nitro-1,2-benzisothiazole

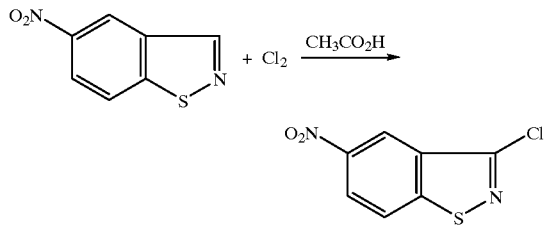

A suspension of 5-nitro-1,2-benzisothiazole (271 g, 1.50 mol) in acetic acid is heated to 80° C. to form a solution. The heating source is removed and chlorine gas is added continuously over six hours at 70–80° C. until saturation of the mixture occurs. The mixture is cooled to room temperature and stirred overnight. Filtration affords the title compound as a yellow crystalline solid (237 g, 73.6%) which is identified by NMR spectral analysis.

EXAMPLE 40

Preparation of 2'-Chloro-2-methyl-2-carboethoxy propiophenone

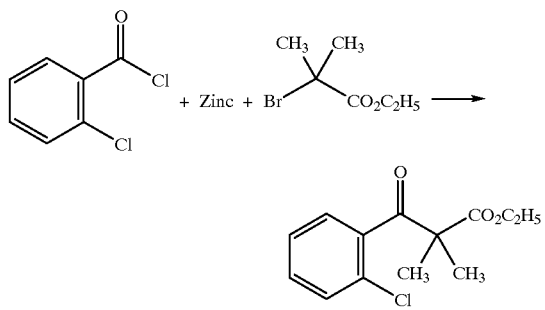

A mixture of 2-chlorobenzoyl chloride (52.2 g, 0.298 mol), ethyl 2-bromoisobutyrate (58.2 g, 0.298 mol) and ether is added in portions to zinc foil (19.5 g, 0.298 mol) and the resultant mixture stirred at reflux for three hours and overnight at room temperature. The mixture is poured into cold, dilute sulfuric acid and the organic layer is washed with saturated sodium bicarbonate and brine, dried over anhydrous magnesium sulfate and concentrated in vacuo to a yellow oil. The oil is chromatographed on silica gel with hexanes:ethyl acetate to afford the title compound as a colorless oil (41.8 g, 55.1%).

EXAMPLE 41

Preparation of 2'-Chloro-5'-nitro-2-methyl-2-carboethoxypropiophenone

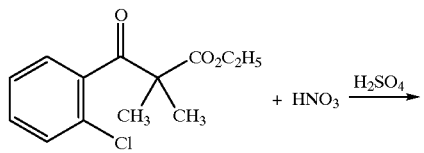

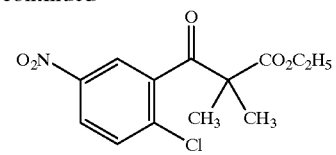

To concentrated sulfuric acid (15.0 ml) at 5° C. is added 2'-chloro-2-methyl-2-carboethoxypropiophenone (4.00 g, 0.01570 mol) followed by dropwise addition of concentrated nitric acid (90%, 0.740 ml, 0.0204 mol). After stirring 5 minutes, the mixture is poured onto ice and extracted with ethyl acetate. The organic layers are washed with saturated sodium bicarbonate and brine, dried over anhydrous magnesium sulfate, filtered and concentrated in vacuo to afford the title compound as a yellow oil (3.90 g, 83.0%) which is identified by NMR spectral analysis.

EXAMPLE 42

Preparation of 1-Benzothiophen-2,3-dione

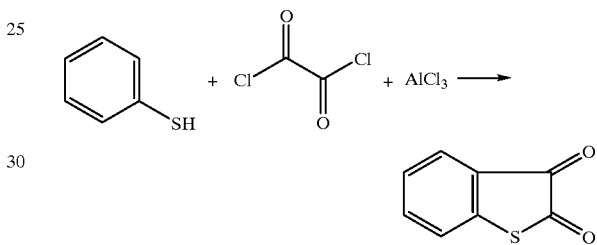

To a solution of thiophenol (100 g, 0.907 mol) in ether is added dropwise a solution of oxalyl chloride (175 g, 1.38 mol) in ether. The mixture is stirred two hours at reflux and concentrated in vacuo. The residue is taken up in methylene chloride and cooled to 0° C. Aluminum chloride (145 g, 1.09 mol) is added in portions such that the temperature does not exceed 25° C. The resultant mixture is stirred 30 minutes at reflux, cooled to room temperature and poured into ice water with stirring. The organic layer is washed with saturated sodium bicarbonate, water and brine, dried over anhydrous magnesium sulfate, filtered and concentrated in vacuo to an orange solid which is recrystallized from methylene chloride:hexanes to afford the title compound (102 g, 69.0%) which is identified by NMR spectral analysis.

EXAMPLE 43

Preparation of 1,2-Benzisothiazole-3-carboxamide

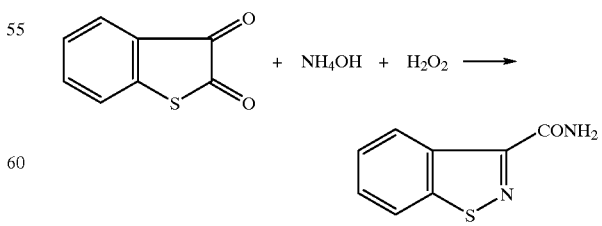

To ammonium hydroxide (1.78 l) is added 1-benzothiophen-2,3-dione (87.0 g, 0.530 mol) at 5–10° C., followed by hydrogen peroxide (30% aqueous, 178 ml). The resultant mixture is filtered to obtain a yellow solid which is dried (77.0 g, 81.7%) and identified as the title compound by NMR and IR spectral analysis.

EXAMPLE 44

Preparation of 3-Cyano-5-nitro-1,2-benzisothiazole

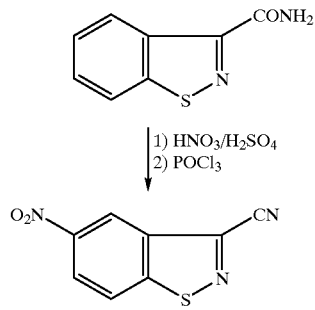

A solution of 1,2-benzisothiazole-3-carboxamide (12.0 g, 0.0674 mol) in concentrated sulfuric acid at 0–5° C. is treated dropwise with nitric acid (90%, 4.12 ml) such that the temperature does not exceed 10° C., stirred one hour at 5° C., and poured into ice water with vigorous stirring. The resultant suspension is filtered to obtain a solid. The solid is dried and recrystallized from acetonitrile to afford a white solid (10.0 g) which is treated with phosphorus oxychloride (60.0 ml). The resultant mixture is stirred at 90–100° C. for 90 minutes, cooled to room temperature, slowly poured into ice water with stirring, and filtered to obtain a solid. Recrystallization of the solid from methylene chloride:hexanes gives the title compound as an orange solid (8.00 g, 87.9%, mp 168–170° C.) which is identified by NMR and IR spectral analyses.

EXAMPLE 45

Preparation of 2,4-Difluoro-5-nitrobenzoyl Chloride

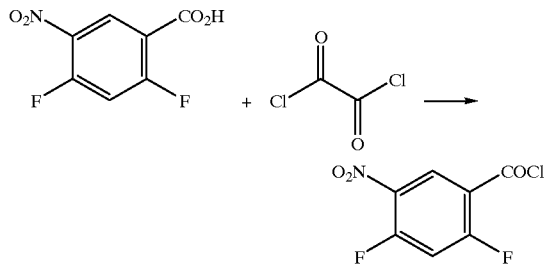

Oxalyl chloride (94.0 g, 0.739 mol) is added dropwise to a mixture of 2,4-difluoro-5-nitrobenzoic acid (100.0 g, 0.492 mol), methylene chloride and N,N-dimethylformamide (0.600 ml). The resultant mixture is stirred 3.25 hours at reflux, cooled to room temperature, and concentrated in vacuo to afford the title compound as a brown oil (111 g, 95.2%).

EXAMPLE 46

Preparation of 3-(6-Methoxy-m-tolyl)-6-amino-5-nitro-1,2-benzisothiazole

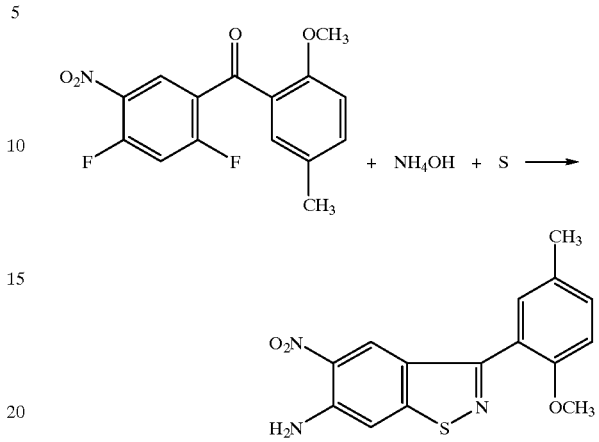

Ammonium hydroxide (330 ml) is added to a suspension of 2',4'-difluoro-2-methoxy-5-methyl-5'-nitrobenzophenone (60.0 g, 0.186 mol), sulfur (6.25 g, 0.195 mol) and N,N-dimethylformamide on an ice bath. The resultant mixture is allowed to warm to 35° C., heated gradually to 81° C. over a two hour period, cooled to room temperature, and poured into water. The resultant solid is taken up in ethyl acetate and N,N-dimethylformamide, and washed with water. The organic layer is concentrated in vacuo to afford the title compound which is identified by NMR spectral analysis.

EXAMPLE 47

Preparation of 3-(6-Methoxy-m-tolyl)-6-chloro-5-nitro-1,2-benzisothiazole

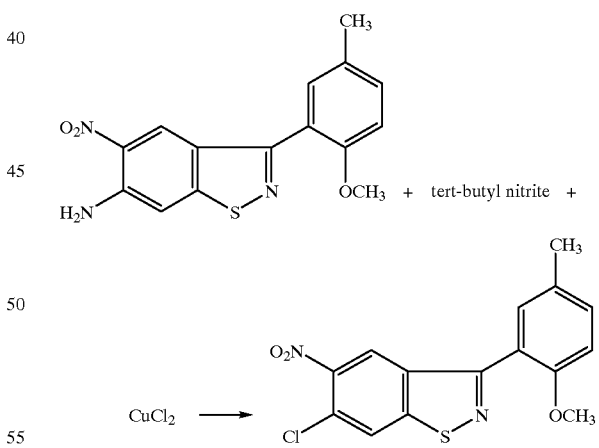

A mixture of tert-butyl nitrite (5.90 g, 0.0571 mol), copper chloride (6.20 g, 0.0457 mol) and acetonitrile is heated to 65–75° C., treated with 3-(6-methoxy-m-tolyl)-6-amino-5-nitro-1,2-benzisothiazole (12.0 g, 0.0381 mol) over 10 minutes, stirred for two hours at 67–75° C., treated with tert-butyl nitrite (1.50 ml) and copper chloride (1.00 g), stirred 40 minutes at 67–75° C., cooled to room temperature, and diluted with ethyl acetate. The organic layer is washed with 10% hydrochloric acid and filtered. The filtrate is washed with water and concentrated in vacuo to afford the title compound as a solid (10.6 g, 83.1%) which is identified by NMR and IR spectral analyses.

EXAMPLE 48

Preparation of 3-(6-Methoxy-m-tolyl)-6-fluoro-5-nitro-1,2-benzisothiazole

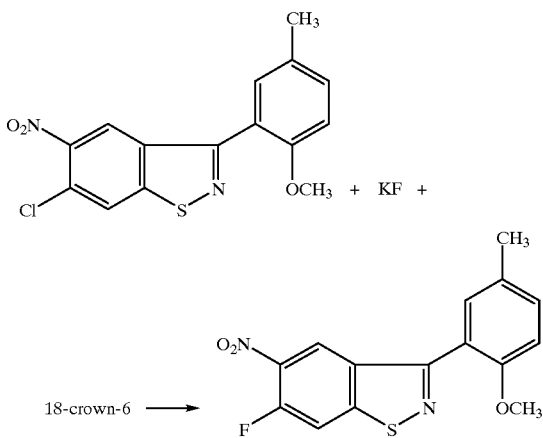

A mixture of 3-(6-methoxy-m-tolyl)-6-chloro-5-nitro-1,2-benzisothiazole (7.30 g, 0.0218 mol), potassium fluoride (6.33 g, 0.109 mol) 18-crown-6 (2.31 g, 0.0872 mol) and sulfolane is stirred 19 hours at 154° C., cooled to room temperature, and poured into ice water. The resultant solid is filtered and chromatographed on silica gel with methylene chloride to afford a solid which is recrystallized from acetonitrile to afford a tan powder. The powder is recrystallized from ethyl acetate to give the title compound as a tan solid (2.09 g, 29.9%) which is identified by NMR spectral analysis.

EXAMPLE 49

Preparation of 5-Amino-4-bromo-6-fluoro-3-methyl-1,2-benzisothiazole

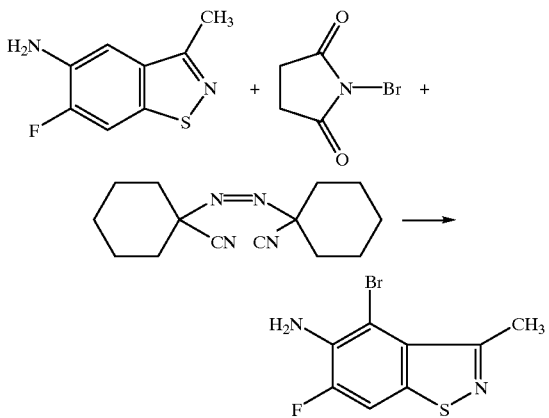

To a solution of 5-amino-6-fluoro-3-methyl-1,2-benzisothiazole (0.600 g, 0.00329 mol) in 1,2-dichloroethane is added N-bromosuccinimide (0.586 g, 0.00329 mol) followed by 1,1'-azobis(cyclohexanecarbonitrile) (0.0200 9). The mixture is stirred two hours at 70° C., additional N-bromosuccinimide (0.240 g, 0.00135 mol) is added, and the mixture is stirred 40 minutes at 70° C. The mixture is then cooled to room temperature, filtered and concentrated in vacua to obtain a residue. The residue is chromatographed on silica gel to give the title compound (0.870 g, 100%) which is identified by NMR spectral analysis.

We claim:

1. A process for the preparation of a 6-(perfluoroalkyl) uracil compound having the structural formula I

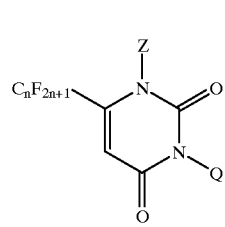

wherein
n is an integer of 1,2,3,4,5 or 6;
Z is hydrogen or $C_1$–$C_6$alkyl; and
Q is a $C_1$–$C_6$alkyl group or

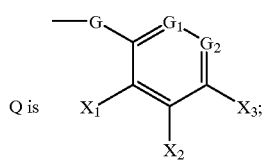

where
G is $CH_2$ or a bond;
$G_1$ is $CX_5$ or N;
$G_2$ is $CX_4$ or N;
$X_1$ is hydrogen, halogen or a $C_1$–$C_6$alkyl group optionally substituted with one epoxy group,
$X_2$ is hydrogen, halogen, $NRR_1$, $CO_2R_2$, $C(O)R_3$, $OR_4$, $SO_2R_5$, $SO_2NR_6R_7$, $C(R_8)(OR_9)_2$, $C(R_{10})$=$NOR_{11}$, $C(R_{12})$=$C(R_{13})$—$C(OR_{14})$=$NOR_{15}$, $CH_2O$—$NCO_2R_{16}$,
1,3-dioxolane optionally substituted with one
   $C_1$–$C_6$alkoxy group or one or two $C_1$–$C_4$alkyl groups,
1,3-dioxolinone optionally substituted with one
   $C_{1-6}$alkoxy group or one or two $C_1$–$C_4$alkyl groups, or
$C_1$–$C_4$alkyl optionally substituted with one $CO_2R_2$ group and one halogen atom, and
$X_3$ is hydrogen, halogen, $C_1$–$C_4$haloalkyl, $CO_2R_{17}$, cyano, $C_1$–$C_4$haloalkoxy, $OR_{18}$ or $C_1$–$C_4$alkyl, or
when $X_1$ and $X_2$ are taken together with the atoms to which they are attached, they may form a five- or six-membered ring wherein $X_1X_2$ or $X_2X_1$ is represented by:
—OC($R_{20}$)($R_{21}$)O—, —$CH_2S(O)_pN(R_{22})$—, —SC($R_{23}$)=N—, —CH=CH—CH($R_{11}$)O—, —OC(O)N—, —SC($R_{24}$)=N—, —ON($R_{25}$)C(O)—, —OC(CO$_2R_{26}$)=C($R_{27}$)—, —NC($R_{28}$)=C(SR$_{29}$)—, —CH=C(CO$_2R_{30}$)O—, —CH$_2$CH($R_{31}$)O— or —OC($R_{32}$)($R_{33}$)C(O)—, or
when $X_2$ and $X_3$ are taken together with the atoms to which they are attached, they may form a five- or six-membered ring wherein $X_2X_3$ or $X_3X_2$ is represented by:

—NC($R_{34}$)=NC(S)—, —N($R_{35}$)N=C($R_{36}$)—,
—N($R_{37}$)C($R_{38}$)=N—, —N($R_{38}$)C(O)CH$_2$O—,
—N($R_{39}$)C(O)CH=CH—, —S—N=C($R_{40}$)—,
—O—N=C($R_{41}$)—, —N=N—N($R_{42}$)—,
—C($R_{43}$)($R_{44}$)C(O)N($R_{45}$)— or —N($R_{46}$)C(O)C($R_{47}$)($R_{48}$)—, $X_4$ is hydrogen, halogen or $OR_{19}$;

$X_5$ is hydrogen or halogen;

R, $R_{56}$, $R_{64}$, $R_{69}$, $R_{70}$, $R_{77}$ and $R_{91}$ are each independently hydrogen, $SO_2R_{49}$, $C_1$–$C_4$alkyl, $C_3$–$C_7$cycloalkyl, $C_3$–$C_6$alkenyl, $C_3$–$C_6$alkynyl, phenyl or benzyl;

$R_1$ is hydrogen, $SO_2R_{50}$, $C(O)R_{51}$, amino or $C_1$–$C_4$alkyl optionally substituted with $CO_2R_{52}$ or $C(O)R_{53}$;

$R_2$, $R_{16}$, $R_{17}$, $R_{26}$, $R_{30}$, $R_{68}$, $R_{75}$, $R_{76}$, $R_{82}$ and $R_{88}$ are each independently hydrogen, $C_1$–$C_8$haloalkyl, $C_3$–$C_8$alkenyl, $C_3$–$C_6$alkynyl, phenyl, benzyl, furfuryl, pyridyl, thienyl,
  $C_1$–$C_8$alkyl optionally substituted with $CO_2R_{54}$, morpholine or $C(O)R_{55}$, or
  an alkali metal, an alkaline earth metal, ammonium or organic ammonium cation;

$R_3$, $R_{66}$, $R_{67}$, $R_{81}$, $R_{85}$ and $R_{89}$ are each independently hydrogen, $C_1$–$C_6$alkyl, $C_3$–$C_6$alkenyl, $C_3$–$C_6$alkynyl, $NR_{56}R_{57}$, phenyl or benzyl;

$R_4$, $R_{18}$, $R_{19}$ and $R_{65}$ are each independently hydrogen, $C_1$–$C_6$alkyl, $C_3$–$C_6$alkenyl, $C_3$–$C_6$alkynyl, $C_1$–$C_4$haloalkyl, $C(O)R_{58}$, $C(S)R_{59}$ or benzyl;

$R_5$ and $R_{72}$ are each independently $C_1$–$C_6$alkyl, $C_1$–$C_6$haloalkyl, $NR_{60}R_{61}$, imidazole or indazole;

$R_6$, $R_{11}$, $R_{12}$, $R_{14}$, $R_{15}$, $R_{20}$, $R_{21}$, $R_{22}$, $R_{25}$, $R_{28}$, $R_{29}$, $R_{31}$, $R_{32}$, $R_{33}$, $R_{35}$, $R_{45}$, $R_{46}$, $R_{63}$ and $R_{80}$ are each independently hydrogen or $C_1$–$C_4$alkyl;

$R_7$ is hydrogen, $C_3$–$C_6$alkenyl, $C_3$–$C_6$alkynyl, benzyl, or $C_1$–$C_4$alkyl optionally substituted with cyano or $C(O)R_{62}$;

$R_8$ and $R_{27}$ are each independently hydrogen, $C_1$–$C_4$alkyl or $C_1$–$C_4$alkoxy;

$R_9$ and $R_{90}$ are each independently $C_1$–$C_6$alkyl;

$R_{10}$ is hydrogen, $C_1$–$C_6$alkyl, phenyl or benzyl;

$R_{13}$, $R_{24}$ and $R_{36}$ are each independently hydrogen, $C_1$–$C_6$alkyl or halogen;

$R_{23}$ is hydrogen or $NR_{63}R_{64}$;

$R_{34}$ is hydrogen, $C_1$–$C_4$alkyl or $C_1$–$C_4$haloalkyl;

$R_{37}$ is hydrogen, $C_1$–$C_4$alkyl or $C_2$–$C_8$alkoxyalkyl;

$R_{38}$ and $R_{39}$ are each independently hydrogen, $C_1$–$C_4$alkyl, $C_1$–$C_4$haloalkyl, $C_3$–$C_6$alkenyl or $C_3$–$C_6$alkynyl;

$R_{40}$, $R_{41}$ and $R_{42}$ are each independently hydrogen, halogen, cyano, $OR_{65}$, $C(O)R_{66}$, $C(S)R_{67}$, $CO_2R_{68}$, $C(=NOR_{69})$,
  a $C_1$–$C_8$alkyl, $C_3$–$C_7$cycloalkyl, $C_2$–$C_8$alkenyl or $C_2$–$C_8$alkynyl group, wherein each group is optionally substituted with any combination of one to six halogen atoms, one to three $C_1$–$C_{10}$alkoxy groups, one or two $C_1$–$C_6$haloalkoxy groups, one or two $NR_{70}R_{71}$ groups, one or two $S(O)_qR_{72}$ groups, one or two cyano groups, one or two $C_3$–$C_7$cycloalkyl groups, one $OSO_2R_{73}$ group, one or two $C(O)R_{74}$ groups, one or two $CO_2R_{75}$ groups, one or two $C(O)SR_{76}$ groups, one or two $C(O)NR_{77}R_{78}$ groups, one to three $OR_{79}$ groups, one or two $P(O)(OR_{80})_2$ groups, one 1,3-dioxolane optionally substituted with one to three $C_1$–$C_4$alkyl groups, or one 1,3-dioxane optionally substituted with one to three $C_1$–$C_4$alkyl groups, or phenyl or benzyl optionally substituted with any combination of one to three halogen atoms, one to three $C_1$–$C_6$alkyl groups, one to three $C_1$–$C_6$alkoxy groups, one $C_3$–$C_7$cycloalkyl group, one $C_1$–$C_4$haloalkyl group, one $C_1$–$C_4$alkylthio group, one cyano group, one nitro group, one $C(O)R_{81}$ group, one $CO_2R_{82}$ group, one $OR_{83}$ group, one $SR_{84}$ group, one $C_1$–$C_6$alkoxymethyl group, one hydroxymethyl group, one $C_3$–$C_8$alkenyloxymethyl group, or one $C_1$–$C_8$haloalkoxymethyl group;

$R_{43}$, $R_{44}$, $R_{47}$ and $R_{48}$ are each independently hydrogen, $C_1$–$C_4$alkyl, $C_1$–$C_4$haloalkyl, $C_3$–$C_6$alkenyl, $C_3$–$C_6$alkynyl or $C_3$–$C_7$cycloalkyl, or $R_{43}$ and $R_{44}$ or $R_{47}$ and $R_{48}$ may be taken together with the atom to which they are attached to form a $C_3$–$C_7$cycloalkyl group;

$R_{49}$, $R_{50}$ and $R_{86}$ are each independently $C_1$–$C_6$alkyl, $NR_{93}R_{94}$, $C_1$–$C_4$haloalkyl, $C_3$–$C_6$alkenyl, $C_3$–$C_6$alkynyl or benzyl;

$R_{51}$, $R_{52}$, $R_{53}$, $R_{54}$, $R_{55}$, $R_{56}$, $R_{57}$, $R_{58}$, $R_{60}$, $R_{61}$, $R_{62}$, $R_{71}$, $R_{73}$, $R_{74}$, $R_{78}$, $R_{87}$ and $R_{92}$ are each independently hydrogen, $C_1$–$C_6$alkyl, $C_3$–$C_7$cycloalkyl, $C_1$–$C_6$haloalkyl, $C_3$–$C_6$alkenyl, $C_3$–$C_6$alkynyl, phenyl or benzyl;

$R_{79}$, $R_{83}$ and $R_{84}$ are each independently hydrogen, $C(O)R_{85}$, $SO_2R_{86}$, $C_1$–$C_6$haloalkyl, $C_2$–$C_6$alkenyl, $C_5$–$C_8$cycloalkenyl, $C_2$–$C_6$alkynyl, phenyl, benzyl, or $C_1$–$C_{10}$alkyl optionally substituted with one hydroxyl, benzyloxy, $OC(O)R_{87}$, $C_1$–$C_6$alkoxy, $CO_2R_{88}$, $C(O)R_{89}$, $C(OR_{90})_2$, $C(O)NR_{91}R_{92}$ or cyano group;

$R_{93}$ and $R_{94}$ are each independently hydrogen, $C_1$–$C_4$haloalkyl, $C_2$–$C_6$alkenyl, $C_3$–$C_8$cycloalkyl,
  $C_1$–$C_8$alkyl optionally substituted with one or two $C_1$–$C_4$alkoxy groups or one cyanoalkyl group, or
  benzyl or phenyl optionally substituted with any combination of one to three halogen atoms, one to three $C_1$–$C_4$alkyl groups, one to three $C_1$–$C_4$haloalkyl groups, one to three $C_1$–$C_4$alkoxy groups, one to three $C_1$–$C_4$haloalkoxy groups, one cyano group or one nitro group, and
  when $R_{93}$ and $R_{94}$ are taken together with the nitrogen atom to which they are attached, they form a 5- to 12-membered monocyclic or fused bicyclic, heterocyclic ring optionally substituted with one or more groups independently selected from halogen, cyano, nitro, amino, hydroxyl, $C_1$–$C_4$alkyl, $C_1$–$C_4$haloalkyl, $C_1$–$C_4$alkoxy, $C_1$–$C_4$haloalkoxy and $C_1$–$C_4$haloalkylsulfonyl groups; p and q are each independently 0, 1 or 2;

which process comprises:
(a) reacting a 2-(N,N-disubstituted)amino-4-(perfluoroalkyl)-1,3-oxazin-6-one compound having the structural formula II

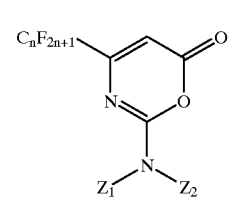

(II)

wherein
  $Z_1$ and $Z_2$ are each independently $C_1$–$C_8$alkyl or $Z_1$ and $Z_2$ may be taken together with the atom to which they are attached to form a 4- to 7-membered ring wherein $Z_1Z_2$ is represented by $-(CH_2)_2O(CH_2)_2-$ or $-(CH_2)_m-$ where m is an integer of 3, 4, 5 or 6; and n is as described above, with an amine compound having the structural formula III $$QNH_2 \quad (III)$$

wherein Q is as described above, in the presence of an acid or base to form the 6-(perfluoroalkyl)uracil compound of formula I wherein Z is hydrogen; and (b) optionally alkylating the formula I compound wherein Z is hydrogen to form a formula I compound wherein Z is $C_1-C_6$ alkyl.

2. The process according to claim 1 wherein the reaction of step (a) occurs in the presence of an acid.

3. The process according to claim 2 wherein the acid is selected from the group consisting of a $C_1-C_6$alkanoic acid, hydrochloric acid, sulfuric acid and phosphoric acid.

4. The process according to claim 2 wherein the acid is selected from the group consisting of acetic acid and propionic acid.

5. The process according to claim 1 wherein the base is selected from the group consisting of a tri-($C_1-C_6$alkyl) amine, a heterocyclic tertiary amine and an alkali metal $C_1-C_6$alkoxide.

6. The process according to claim 5 wherein the base is selected from the group consisting of 1,8-diazabicyclo [5.4.0]undec-7-ene and 1,5-diazabicyclo-[4.3.0]non-5-ene.

7. The process according to claim 1 wherein the 2-(N,N-disubstituted)amino-4-(perfluoroalkyl)-1,3-oxazin-6-one compound is reacted with the amine compound in the presence of a solvent.

8. The process according to claim 7 wherein the solvent is selected from the group consisting of a carboxylic acid amide, a dialkyl sulfoxide, an aromatic hydrocarbon, a halogenated aromatic hydrocarbon, an aliphatic hydrocarbon, a halogenated aliphatic hydrocarbon, an alkanoic acid, a ketone, an ether, a nitrile and water and mixtures thereof.

9. The process according to claim 1 wherein the 2-(N,N-disubstituted)amino-4-(perfluoroalkyl)-1,3-oxazin-6-one compound is reacted with the amine compound at a temperature of about 20° C. to 150° C.

10. The process according to claim 1 wherein step (b) comprises reacting the formula I compound wherein Z is hydrogen with an alkyl halide having the structural formula IV or a dialkylsulfate ester having the structural formula V $$XZ \quad (IV)$$

or

 (V)

wherein X is chlorine, bromine or iodine, and Z is $C_1-C_6$alkyl in the presence of a base.

11. The process according to claim 1 wherein n is 1;

Z is hydrogen or $C_1-C_4$alkyl;

and $Z_1$ and $Z_2$ are each independently $C_1-C_6$alkyl.

12. The process according to claim 11 wherein

Z is hydrogen or methyl;

$X_1$ is hydrogen, fluorine or $C_1-C_3$alkyl optionally substituted with one epoxy group; or when $X_1$ and $X_2$ are taken together with the atoms to which they are attached, they may form a five- or six-membered ring wherein $X_1X_2$ or $X_2X_1$ is represented by:

$-OC(R_{20})(R_{21})O-$, $-CH_2S(O)_pN(R_{22})-$, $-SC(R_{23})=N-$, $-CH=CH-CH(R_{11})O-$, $-OC(O)N-$, $-SC(R_{24})=N-$, $-ON(R_{25})C(O)-$, $-OC(CO_2R_{26})=CH-$, $-NC(R_{28})=C(SR_{29})-$, $-CH=C(CO_2R_{30})O-$, $-CH_2CH(R_{31})O-$ or $-OC(R_{32})(R_{33})C(O)-$;

R, $R_{64}$, $R_{69}$ and $R_{77}$ are each independently hydrogen, $SO_2R_{49}$ or $C_1-C_4$alkyl;

$R_2$, $R_{16}$, $R_{17}$, $R_{26}$, $R_{30}$, $R_{68}$, $R_{75}$, $R_{76}$, $R_{82}$ and $R_{88}$ are each independently hydrogen, $C_3-C_6$alkenyl or $C_1-C_4$alkyl optionally substituted with $CO_2R_{54}$, morpholine or $C(O)R_{55}$;

$R_3$, $R_{66}$, $R_{67}$, $R_{85}$ and $R_{89}$ are each independently hydrogen, $C_1-C_4$alkyl or $NR_{56}R_{57}$;

$R_4$, $R_{18}$ and $R_{19}$ are each independently hydrogen, $C_1-C_4$alkyl, $C_1-C_4$haloalkyl, $C(O)R_{58}$, $C_3-C_4$alkenyl or $C_3-C_4$alkynyl;

$R_{56}$ is $SO_2R_{49}$;

$R_{57}$ is hydrogen or $C_1-C_4$alkyl;

$R_5$ and $R_{72}$ are each independently $NR_{60}R_{61}$ or indazole;

$R_6$, $R_{11}$, $R_{12}$, $R_{14}$, $R_{15}$, $R_{20}$, $R_{21}$, $R_{22}$, $R_{25}$, $R_{28}$, $R_{29}$, $R_{31}$, $R_{32}$, $R_{33}$, $R_{35}$, $R_{45}$, $R_{46}$ and $R_{80}$ are each independently hydrogen or methyl;

$R_7$ is $C_1-C_4$alkyl optionally substituted with cyano or $C(O)R_{62}$;

$R_8$ is hydrogen or $C_1-C_4$alkoxy;

$R_9$ and $R_{90}$ are each independently $C_1-C_4$alkyl;

$R_{10}$ is hydrogen or $C_1-C_3$alkyl;

$R_{13}$, $R_{24}$ and $R_{36}$ are each independently hydrogen or chlorine;

$R_{23}$ is $NR_{63}R_{64}$;

$R_{34}$ is $C_1-C_3$haloalkyl;

$R_{37}$ is $C_2-C_4$alkoxyalkyl;

$R_{38}$ and $R_{39}$ are each independently $C_1-C_3$haloalkyl, $C_1-C_3$alkyl or propargyl;

$R_{40}$, $R_{41}$, and $R_{42}$ are each independently hydrogen, $C(O)R_{66}$, $C(S)R_{67}$, $CO_2R_{68}$, $C(=NOR_{69})$, $C_1-C_3$alkyl optionally substituted with any combination of one or two halogen atoms, one or two $C_1-C_3$alkoxy groups, one or two $C_1-C_3$haloalkoxy groups, one $SO_2R_{72}$ group, one or two cyano groups, one $C_3-C_5$cycloalkyl group, one $OSO_2R_{73}$ group, one $C(O)R_{74}$ group, one $CO_2R_{75}$ group, one $C(O)SR_{76}$ group, one $C(O)NR_{77}R_{78}$ group, one to two $OR_{79}$ groups, one $P(O)(OR_{80})_2$ group, one 1,3-dioxolane group or one 1,3-dioxane group, or phenyl optionally substituted with any combination of one halogen atom, one or two methyl groups, one methoxy group, one halomethyl group or one $OR_{83}$ group;

$R_{43}$, $R_{44}$, $R_{47}$ and $R_{48}$ are each independently hydrogen or methyl, or $R_{43}$ and $R_{44}$ or $R_{47}$ and $R_{48}$ may be taken together with the atom to which they are attached to form a cyclopropyl group;

$R_{49}$, $R_{50}$ and $R_{86}$ are each independently $C_1-C_4$alkyl or $NR_{93}R_{94}$;

$R_{51}$, $R_{52}$, $R_{53}$, $R_{54}$, $R_{55}$, $R_{58}$, $R_{60}$, $R_{61}$, $R_{62}$, $R_{73}$, $R_{74}$, $R_{78}$ and $R_{87}$
are each independently hydrogen, $C_1$–$C_4$alkyl or $C_1$–$C_4$haloalkyl;

$R_{79}$ and $R_{83}$ are each independently hydrogen, $C(O)R_{85}$, $SO_2R_{86}$, $C_1$–$C_4$haloalkyl, $C_3$–$C_4$alkenyl or
$C_1$–$C_3$alkyl substituted with one $OC(O)R_{87}$, $CO_2R_{88}$, $C(O)R_{89}$, $C(OR_{90})_2$ or cyano group;

$R_{93}$ and $R_{94}$ are each independently hydrogen or $C_1$–$C_8$alkyl;

p is 0, 1 or 2; and $Z_1$ and $Z_2$ are the same and represent methyl or ethyl.

13. The process according to claim 1 for the preparation of a 6-(trifluoromethyl)uracil compound having the structural formula VI

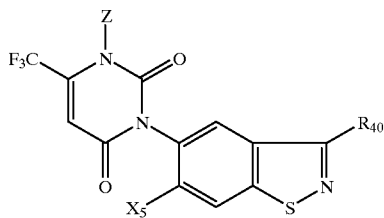

(VI)

wherein

Z is hydrogen or methyl;

$X_5$ is hydrogen or halogen;

$R_{40}$ is hydrogen, $C(O)R_{66}$, $C(S)R_{67}$, $CO_2R_{68}$,
$C_1$–$C_3$alkyl optionally substituted with any combination of one or two halogen atoms, one or two $C_1$–$C_3$alkoxy groups, one or two $C_1$–$C_3$haloalkoxy groups, one $SO_2R_{72}$ group, one or two cyano groups, one $C_3$–$C_5$cycloalkyl group, one $OSO_2R_{73}$ group, one or two $OR_{79}$ groups, one $P(O)(OR_{80})_2$ group, one 1,3-dioxolane group or one 1,3-dioxane group, or phenyl optionally substituted with any combination of one halogen atom, one or two methyl groups, one methoxy group, one halomethyl group or one $OR_{83}$ group;

$R_{66}$, $R_{67}$, $R_{85}$ and $R_{89}$ are each independently hydrogen, $C_1$–$C_4$alkyl or $NR_{56}R_{57}$;

$R_{56}$ is $SO_2R_{49}$;

$R_{57}$ is hydrogen or $C_1$–$C_4$alkyl;

$R_{49}$ and $R_{86}$ are each independently $C_1$–$C_4$alkyl or $NR_{93}R_{94}$;

$R_{93}$ and $R_{94}$ are each independently hydrogen or $C_1$–$C_8$alkyl;

$R_{68}$ and $R_{88}$ are each independently hydrogen, $C_3$–$C_6$alkenyl or
$C_1$–$C_4$alkyl optionally substituted with $CO_2R_{54}$, morpholine or $C(O)R_{55}$;

$R_{54}$, $R_{55}$, $R_{60}$, $R_{61}$, $R_{73}$ and $R_{87}$ are each independently hydrogen, $C_1$–$C_4$alkyl or $C_1$–$C_4$haloalkyl;

$R_{72}$ is $NR_{60}R_{61}$ or indazole;

$R_{79}$ and $R_{83}$ are each independently hydrogen $C(O)R_{85}$, $SO_2R_{86}$, $C_1$–$C_4$haloalkyl, $C_3$–$C_4$alkenyl or
$C_1$–$C_3$alkyl substituted with one $OC(O)R_{87}$, $CO_2R_{88}$, $C(O)R_{89}$, $C(OR_{90})_2$ or cyano group;

$R_{80}$ is hydrogen or methyl; and $R_{90}$ is $C_1$–$C_4$alkyl.

* * * * *